(12) United States Patent
Flohr

(10) Patent No.: US 11,090,513 B2
(45) Date of Patent: Aug. 17, 2021

(54) METHOD FOR TREATING HAIR, KIT, AND USE OF THE KIT

(71) Applicant: COTY INC., New York, NY (US)

(72) Inventor: Andreas Flohr, Kronberg im Taunus (DE)

( * ) Notice: Subject to any disclaimer, the term of this patent is extended or adjusted under 35 U.S.C. 154(b) by 0 days.

(21) Appl. No.: 16/500,630

(22) PCT Filed: Apr. 11, 2018

(86) PCT No.: PCT/US2018/027079
§ 371 (c)(1),
(2) Date: Oct. 3, 2019

(87) PCT Pub. No.: WO2018/191362
PCT Pub. Date: Oct. 18, 2018

(65) Prior Publication Data
US 2020/0094084 A1    Mar. 26, 2020

(30) Foreign Application Priority Data

Apr. 12, 2017 (EP) ..................................... 17166308
Apr. 25, 2017 (EP) ..................................... 17168001

(51) Int. Cl.
| | | |
|---|---|---|
| *A61Q 5/10* | (2006.01) | |
| *A61K 8/362* | (2006.01) | |
| *A61K 8/365* | (2006.01) | |
| *A61Q 5/06* | (2006.01) | |
| *A61Q 5/08* | (2006.01) | |
| *A61Q 5/12* | (2006.01) | |

(52) U.S. Cl.
CPC ................ *A61Q 5/10* (2013.01); *A61K 8/362* (2013.01); *A61K 8/365* (2013.01); *A61K 2800/884* (2013.01); *A61Q 5/065* (2013.01); *A61Q 5/08* (2013.01); *A61Q 5/12* (2013.01)

(58) Field of Classification Search
CPC . A61Q 5/10; A61Q 5/065; A61Q 5/12; A61K 8/365; A61K 8/362; A61K 8/36; A61K 2800/884
USPC ............. 8/405, 202, 208; 132/405, 202, 208
See application file for complete search history.

(56) References Cited

U.S. PATENT DOCUMENTS

| | | |
|---|---|---|
| 2004/0126348 A1 | 7/2004 | Browning |
| 2005/0196369 A1 | 9/2005 | Ueyama |
| 2017/0035175 A1 | 2/2017 | Malle |

FOREIGN PATENT DOCUMENTS

| | | | |
|---|---|---|---|
| DE | 10051774 A1 | 4/2002 | |
| WO | 2017/041907 A1 | 3/2017 | |
| WO | WO 207/041907 A1 * | 3/2017 | ............... A61Q 5/10 |

OTHER PUBLICATIONS

STIC Search Report dated May 28, 2020.*
International Search Report for PCT/US2018/027079.

* cited by examiner

*Primary Examiner* — Eisa B Elhilo
(74) *Attorney, Agent, or Firm* — Egbert, McDaniel & Swartz, PLLC

(57) ABSTRACT

A method, a kit and a first composition for treating hair are provided. The method for treating hair comprises applying to the hair a first composition comprising in a cosmetically acceptable carrier, one or more at least bi-functional carboxylic acids, or cosmetically acceptable salts thereof, or mixtures thereof, and applying to the hair a second composition comprising in a cosmetically acceptable carrier, one or more at least bi-functional carboxylic acids, or cosmetically acceptable salts thereof, or mixtures thereof, wherein the first composition has a pH from 7 to 13 and the second composition has a pH from 3 to 7.

18 Claims, No Drawings

METHOD FOR TREATING HAIR, KIT, AND USE OF THE KIT

CLAIM OF PRIORITY

This patent application is the U.S. National Stage of International Application No. PCT/US2018/027079, filed on Apr. 11, 2018, which claims the benefit of priority to European Application Serial No. 17166308.1, filed Apr. 12, 2017, as well as European Application Serial No. 17168001.0, filed Apr. 25, 2017, which are incorporated by reference herein in their entirety.

FIELD OF THE INVENTION

A method for treating hair is provided and comprises mixing a first composition with a hair treatment composition, applying to the hair the mixed composition; and applying to the hair a second composition. The first and the second composition include in a cosmetically acceptable carrier one or more at least bi-functional carboxylic acids, or cosmetically acceptable salts thereof, wherein the second composition has a pH value of 3 to 7. Also, a kit for treating hair is provided and comprises the first composition and the second composition which are separately packaged. A first composition for treating hair is also provided.

BACKGROUND OF THE INVENTION

Hair coloring or dyeing involves the application of one or more hair dyes onto hair which results in the coloration of hair fibers. The total head of hair color may be changed subtly or dramatically, the root growth colored to match the remaining head of hair, effects introduced such as glitter, hair strand effects or other sectional effects, or the same color "freshened up" to combat fade and/or wash-out.

There is a relative high interest for some clients to get their hair turned super blonde, namely blonde platinum. However, these clients have typically very dark hair. In order to provide the super blonde color, the dark hair needs to be bleached several times. If the hair is already heavily stressed or damaged due to previous bleaching, coloring or dying hair, such bleaching processes are not recommended. The integrity and the healthiness of the client's hair and scalp need always to be preserved and even more improved.

There is also relatively high interest for some clients to permanently change their hair style without changing the color of their hair. This involves client's desire to go from straight to curly hair or, opposite, from curly to straight hair. The first of those style transformations typically involves a reductive hair damage step followed by the mechanical curling of the hair with subsequent oxidation of the hair. If clients desire to change their hair style from curly to straight, typically chemical hair straighteners in combination with excessive heat are being used. As a consequence, permanent waving as well as hair straightening compromises the integrity of clients' hair.

However, there is still a need to provide a method for treating hair in order to improve the integrity and the healthiness of hair when the hair is exposed to relatively heavy stress such as intense bleaching processes, i.e. processes involving a relatively high concentration of oxidizing agents. Suitable compositions for improving the hair quality while simultaneously coloring or bleaching hair should not react with oxidative hair color, should be stable under oxidative conditions, and should not compromise the overall hair color or bleach result.

SUMMARY OF THE INVENTION

According to an embodiment, a method for treating hair may include mixing a first composition which includes one or more at least bi-functional carboxylic acids, or cosmetically acceptable salts thereof, with a hair treatment composition to form a mixed composition. The first composition may have a pH of at least 7. The mixed composition is applied to the hair. A second composition which includes one or more at least bi-functional carboxylic acids, or cosmetically acceptable salts thereof, and which may have a pH lower than 7 is applied to the hair.

According to another embodiment, a method for treating hair includes applying a first composition which includes one or more at least bi-functional carboxylic acids, or cosmetically acceptable salts thereof, to the hair. The first composition has a pH of at least 7. A second composition which includes one or more at least bi-functional carboxylic acids, or cosmetically acceptable salts thereof, and which has a pH lower than 7 is applied to the hair.

According to another embodiment, a method for treating hair includes applying a first composition which includes one or more at least bi-functional carboxylic acids, or cosmetically acceptable salts thereof, to the hair. The first composition has a pH of at least 7. The method further may comprise applying a commercially available hair treatment composition simultaneously with the first composition to the hair or mixing a commercially available hair treatment composition with the first composition prior to applying the first composition to the hair. The commercially available hair treatment composition may comprise at least one of a bleaching agent, a coloring agent, and/or a permanent hair waving agent.

According to an embodiment, a first composition for treating hair is provided. The first composition includes in a cosmetically acceptable carrier one or more at least bi-functional carboxylic acids, or cosmetically acceptable salts thereof, wherein the first composition has a pH value of 7 to 13.

According to an embodiment, a second composition for treating hair is provided. The second composition includes in a cosmetically acceptable carrier one or more at least bi-functional carboxylic acids, or cosmetically acceptable salts thereof, wherein the second composition has a pH value of 3 to 7.

According to an embodiment, a kit includes a first composition and a second composition, wherein the first composition and the second composition are separately packaged. Each of the first and second composition includes one or more at least bi-functional carboxylic acids, or cosmetically acceptable salts thereof. The first composition has a pH of at least 7. The second composition has a pH of less than 7. The kit may further comprise a separately packaged hair treatment composition.

According to another embodiment, a kit includes a first composition and a hair treatment composition, wherein the first composition and the hair treatment composition are separately packaged. The first composition includes one or more at least bi-functional carboxylic acids, or cosmetically acceptable salts thereof. The first composition has a pH of at least 7.

According to an embodiment, the first and the second composition of the kit, or the first composition, are used for restructuring hair or improving stressed hair or structurally damaged hair.

DETAILED DESCRIPTION OF THE INVENTION

Definitions of Terms

In this document, including in all embodiments and aspects of the present invention, the following definitions apply unless specifically stated otherwise.

All percentages are by weight (w/w) of the first composition and/or the second composition, unless otherwise specified. All ratios are weight ratios. "% wt." means percentage by weight. References to 'parts' e.g. a mixture of 1 part X and 3 parts Y, is a ratio by weight. When more than one composition are used during a treatment, the total weight to be considered is the total weight of all the compositions applied on the hair simultaneously (i.e. the weight found "on head"), typically resulting from mixing an oxidative composition (also called developer and/or oxidizing composition/component) with a dye composition (also called tint, and/or dye composition/component), unless otherwise specified. All ratios or percentages are weight ratios or weight percentages unless specifically stated otherwise.

"QS" or "QSP" means sufficient quantity for 100% or for 100 g. "+/−" indicates the standard deviation. All ranges are inclusive and combinable. The number of significant digits conveys neither a limitation on the indicated amounts nor on the accuracy of the measurements. All numerical amounts are understood to be modified by the word "about".

All measurements are understood to be made at 20° C. and at ambient conditions, where "ambient conditions" means at 1 atmosphere (atm) of pressure and at 65% relative humidity, unless otherwise stated. "Relative humidity" refers to the ratio (stated as a percent) of the moisture content of air compared to the saturated moisture level at the same temperature and pressure. Relative humidity can be measured with a hygrometer, in particular with a probe hygrometer from VWR® International.

Herein "min" means "minute" or "minutes". Herein "mol" means mole. Herein "g" following a number means "gram" or "grams". "Ex." means "example". All amounts as they pertain to listed ingredients are based on the active level ('solids') and do not include carriers or by-products that may be included in commercially available materials.

Herein, "comprising" or "including" means that other steps and other ingredients can be present in addition. "Comprising" and "including" encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein. Embodiments and aspects described herein may comprise or be combinable with elements, features or components of other embodiments and/or aspects despite not being expressly exemplified in combination, unless an incompatibility is stated.

Where amount ranges are given, these are to be understood as being the total amount of said ingredient in the composition, or where more than one species fall within the scope of the ingredient definition, the total amount of all ingredients fitting that definition, in the composition.

For example, if the composition comprises from 1% to 5% fatty alcohol, then a composition comprising 2% stearyl alcohol and 1% cetyl alcohol and no other fatty alcohol, would fall within this scope.

The amount of each particular ingredient (e.g. a primary intermediate, a coupler, an oxidizing agent, etc) or mixtures thereof described hereinafter can account for up to 100% (or 100%) of the total amount of the ingredient(s) in the first composition and/or the second composition.

The term "substantially free of" as used herein means less than 1%, less than 0.8%, less than 0.5%, less than 0.3%, or less than an immaterial amount of by total weight of the composition.

The term "free of" as used herein means less than 0.005%, in particular less than 0.001%, by total weight of the composition.

The term "oxidizing agent" is used herein in the usual meaning, and interchangeable with the term "bleaching agent". For example, when the first composition is mixed with an oxidizing agent, the oxidizing agents may be provided in aqueous solution or as a powder which is dissolved prior to use. In one specific embodiment, 0.35 to 1.65 parts by weight, such as one part by weight of the first composition is mixed with 5 parts by weight of commercially available Bleach powder such as for example the powder marketed by Wella under the brand name BLONDOR Multi Blonde Powder and 7.5 parts by weight of a commercially available 9% Hydrogen peroxide solution such as for example the solution marketed by Wella under the brand name BLONDOR Freelights. The mixing ratio of bleach powder to hydrogen peroxide solution typically is 1 to 1.5. Giving a specific example, 2 g to 10 g, such as 6 g of the first composition are mixed with a mix of 45 g Bleach powder plus 30 g hydrogen peroxide solution. Professional hairdressers determine the amount of mixed composition applied to hair as well as the concentration of hydrogen peroxide depending on the damage levels of client's hair and client's hair length.

The term "coloring agent" is used herein in the usual meaning. For example, when the first composition is mixed with a coloring composition, the coloring composition may comprise an oxidative dye precursor, a direct dye, a pigment or a combination thereof. In one specific embodiment, 0.5 to 2.5 parts by weight, such as one part by weight of the first composition is mixed with 7.5 parts by weight of a commercially available crème hair color such as for example the composition marketed by Wella under the brand name KOLESTON Perfect and 7.5 parts by weight of a commercially available 6% Hydrogen peroxide solution such as for example the composition marketed by Wella under the brand name WELLOXON Perfect 6%. The mixing ratio of the crème color comprising the coloring agent or agents to hydrogen peroxide solution typically is 1 to 1. Giving a specific example, 2 g to 10 g, such as 4 g of the first composition are mixed with the crème color comprising the coloring agent or agents. Professional hairdressers determine the amount of mixed composition applied to hair as well as the concentration of hydrogen peroxide depending on the damage levels of client's hair and client's hair length.

The term "permanent hair waving agent" is used herein in the usual meaning. For example, when the first composition is mixed with a permanent hair waving composition, the permanent hair waving composition maybe a water based solution of Thioglycolic Acid or of a cosmetically acceptable salt thereof. In one specific embodiment, 0.65 to 1.35 parts by weight, such as one part by weight of the first composition is mixed with 10 parts by weight of a commercially available permanent hair waving composition, such as for example the composition marketed by Wella under the brand name CURL IT BASELINE. The mixing ratio of the permanent hair waving composition to the first composition is typically 10 to 1. Giving a specific example, 5 g to 10 g, such as 7.5 g of the first composition are mixed with the permanent hair waving composition comprising the permanent hair waving agent. Professional hairdressers determine the amount of mixed composition applied to hair as well as the strength of the permanent hair waving composition, thus the concentration of the permanent hair waving agent in the permanent hair waving composition, depending on the damage levels of client's hair and client's hair length.

The term "cosmetically acceptable salt" as used herein refers to conventional base-addition salts formed from suitable organic or inorganic bases. Sample base-addition salts include those derived from sodium, potassium, ammonium, calcium, magnesium, iron, zinc, zirconium and aluminum hydroxide. Chemical modification of a compound bearing a carboxylic acid function into the corresponding carboxylate salt is a technique well known in the art.

The term "viscosity" as used herein is measured at 25° C. using a HAAKE Rotation Viscometer VT 550 with cooling/heating vessel and sensor systems according to DIN 53019 at a shear rate of 12.9 $s^{-1}$.

The term "kit" as used herein means a packaging unit comprising a plurality of components i.e. a kit of parts. An example of a kit is, for example, a first composition and a separately packaged second composition. Another kit may comprise application instructions comprising a method and a composition.

The term "alkyl" as used herein refers to a saturated straight or branched carbon chain. Unless specified otherwise, the alkyl group can have from 1 to 30 carbon atoms, or particularly from 1 to 12 carbon atoms, or more particularly from 1 to 6 carbon atoms. The alkyl groups may also contain one or more heteroatoms within the carbon backbone. Examples include oxygen, nitrogen, sulfur, and combinations thereof. The alkyl group may particularly contain between one and four heteroatoms. The alkyl groups may include straight-chain alkyl or branched-chain alkyl.

The term "alkyl" includes both "unsubstituted alkyls" and "substituted alkyls", the latter of which refers to alkyl moieties having one or more substituents replacing a hydrogen on one or more carbons of the hydrocarbon backbone. Such substituents may include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, a phosphinate, amino, amido, amidine, imine, cyano, nitro, azido, sulfhydryl, alkylthio, sulfate, sulfonate, sulfamoyl, sulfonamido, sulfonyl, heterocyclyl, aralkyl, or an aromatic or heteroaromatic moiety.

The term "alkenyl" as used herein is an alkyl containing from 2 to 30 carbon atoms and having one or more double bonds. The alkenyl groups may also contain one or more heteroatoms within the carbon backbone. Examples include oxygen, nitrogen, sulfur, and combinations thereof. The alkenyl group may particularly contain between one and four heteroatoms. The alkenyl groups may include straight-chain alkenyl or branched-chain alkenyl, or cycloalkenyl groups. The term "alkenyl" includes both "unsubstituted alkenyls" and "substituted alkenyls", the latter of which refers to alkenyl moieties having one or more substituents replacing a hydrogen on one or more carbons of the hydrocarbon backbone. Such substituents may be the one as set out hereinbefore in the definition of the term "alkyl".

The term "alkynyl" as used herein is an alkyl containing from 2 to 30 carbon atoms and having one or more triple bonds. The alkynyl groups may also contain one or more heteroatoms within the carbon backbone. Examples include oxygen, nitrogen, sulfur, and combinations thereof. The alkenyl group may particularly contain between one and four heteroatoms. The alkynyl groups may include straight-chain alkynyl or branched-chain alkynyl, or cycloalkynyl groups. The term "alkynyl" includes both "unsubstituted alkynyls" and "substituted alkynyls", the latter of which refers to alkynyl moieties having one or more substituents replacing a hydrogen on one or more carbons of the hydrocarbon backbone. Such substituents may be the one as set out hereinbefore in the definition of the term "alkyl".

The term "cycloalkyl" as used herein represents a cyclic version of "alkyl". The term "cycloalkyl" is also meant to include bicyclic, tricyclic and polycyclic versions thereof. Unless specified otherwise, the cycloalkyl group can have 3 to 12 carbon atoms. By analogy, the term "cycloalkenyl" as used herein represents a cyclic version of "alkenyl". The term "cycloalkynyl" as used herein represents a cyclic version of "alkynyl".

The term "alkylene" as used herein denotes the divalent radical derived from a straight or branched alkyl moiety, which alkyl moiety optionally may be substituted. The divalent radical —CH2-CH2-CH2- is an example for an "alkylene". C2-C4 alkylenes include the divalent radicals derived from ethyl, (iso)propyl and (iso)butyl.

The term "cycloalkylene" as used herein denotes the divalent radical derived from a cyclic saturated aliphatic ring structure optionally bearing one or more straight or branched alkyl moieties. The "cycloalkylene" optionally may be substituted either at the cyclic ring structure, at one or more of the optional alkyl moieties, or a combination thereof.

The term "alkenylene" as used herein denotes the divalent radical derived from a straight or branched alkenyl moiety, which alkenyl moiety optionally may be substituted.

The term "(alkyl)arylene" as used herein denotes the divalent radical derived from an aromatic ring or aromatic ring structure optionally bearing one or more straight or branched alkyl moieties. The "(alkyl)arylene" optionally may be substituted either at the aromatic ring or aromatic ring structure, at one or more of the optional alkyl moieties, or a combination thereof.

The term "heterocyclyl" as used herein refers to a cyclic radical attached via a ring carbon or nitrogen of a monocyclic or bicyclic ring containing 3-10 ring atoms, or particularly from 5-6 ring atoms, containing carbon and one to four heteroatoms each selected from oxygen, sulfur, and N(Y) wherein Y is absent or is hydrogen, oxygen, ($C_{1-4}$) alkyl, phenyl or benzyl, and optionally containing one or more double or triple bonds, and optionally substituted with one or more substituents. Examples of heterocyclic ring include, but are not limited to, benzimidazolyl, benzofuranyl, decahydroquinolinyl, 2H,6H-1,5,2-dithiazinyl, dihydrofuro[2,3-b]tetrahydrofuran, imidazolidinyl, imidazolinyl, morpholinyl, octahydroisoquinolinyl, oxazolidinyl, piperazinyl, piperidinyl, piperidonyl, 4-piperidonyl, pyranyl, pyrazolidinyl, pyrazolinyl, pyrrolidinyl, pyrrolinyl, 2H-pyrrolyl, quinuclidinyl and tetrahydrofuranyl.

The term "halogen" as used herein represents fluorine, chlorine, bromine and iodine.

The term "aryl" as used herein refers to an aromatic monocyclic ring containing 6 carbon atoms, an aromatic bicyclic ring system containing 10 carbon atoms or an aromatic tricyclic ring system containing 14 carbon atoms. Examples are phenyl, naphthyl, phenoxathinyl, piperonyl or anthracenyl, particularly phenyl.

The term "heteroaryl" as used herein refers to from three to ten-membered aromatic ring, particularly a five- or six-membered aromatic ring wherein one or more of the carbon atoms in the ring have been replaced by 1, 2, 3, or 4 (for the five-membered ring) or 1, 2, 3, 4, or 5 (for the six-membered ring) of the same or different heteroatoms, whereby the heteroatoms are selected from the group consisting thereof oxygen, nitrogen, sulfur and mixtures thereof. Examples of the heteroaryl group include groups based on pyrrole, furan, imidazole, pyrazole, oxazole, thiazole, and pyridine. Examples of heteroaryl groups may also include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, chromanyl, chromenyl, cinnolinyl, furanyl, furazanyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, naphthyridinyl, oxadiazolyl, 1,2,3-oxadiazolyl, 1,2,4-oxadiazolyl, 1,2,5-oxadiazolyl, 1,3,4-oxadiazolyl, oxazolyl, oxindolyl, pyrimidinyl, phenanthridinyl, phenanthrolinyl, phenazinyl, phenothiazinyl, phenoxazinyl, phthalazinyl, pteridinyl, purinyl, pyrazinyl, pyrazolyl, pyridazinyl, pyridooxazolyl, pyridinyl, pyrimidinyl, pyrrolyl, quinazolinyl, quinolinyl, 4H-quinolizinyl, quinoxalinyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl and thienyl.

The term "acyl" as used herein refers to an alkanoyl group which is usually derived from a carboxylic acid. Therefore, it has the formula RC(O)—, where R represents an alkyl group that is attached to the C(O) group with a single bond.

The term "carboxylic acid" as used herein refers to the group —COOH. Unless specified otherwise the term "carboxylic acid" embraces both the free acid and carboxylate salt.

The term "amine" as used herein refers to primary secondary and tertiary amines corresponding to the groups —NH2, —NHR$^1$ and —NR$^1$R$^2$. Compounds comprising one or more quaternized nitrogen atoms are referred to herein as quaternary "ammonium" compounds.

The term "formyl" as used herein refers to the group —C(O)H.

The term "substituted" as used herein refers to refers to all permissible substituents of the compounds described herein. In the broadest sense, the permissible substituents include acyclic and cyclic, branched and unbranched, carbocyclic and heterocyclic, aromatic and nonaromatic substituents of organic compounds. Illustrative substituents include, but are not limited to, halogens, hydroxyl or alkoxy groups, or any other organic groups containing any number of carbon atoms, particularly $C_{1-14}$ carbon atoms, and optionally include one or more heteroatoms such as oxygen, sulfur, or nitrogen grouping in linear, branched, or cyclic structural formats. Heteroatoms, such as nitrogen, may have hydrogen substituents and/or any permissible substituents of organic compounds described herein that satisfy the valences of the heteroatoms. It is understood that the term "substituted" includes the implicit proviso that such substitution is in accordance with permitted valence of the substituted atom and the substituent, and that the substitution results in a stable compound, i.e. a compound that does not spontaneously undergo transformation such as by rearrangement, cyclization, elimination, etc.

The term "polyfunctional molecule" as used herein refers to molecules with more than one functional groups. The functional groups may be the same or different. A functional group can include, but are not limited to alkane, alkene, alkyne, benzene derivative, haloalkane, alcohol, ketone, aldehyde, acyl halide, carbonate, carboxylate, carboxylic acid, ester, alkoxy, ether, heterocyclic, amide, amine, imine, imide, nitrate, nitrile, pyridine, sulfone, sulfoxide. The polyfunctional molecule may particularly contains at least one ionizable functional group capable of forming ionic bonds. The polyfunctional compounds may more particularly contain at least two ionizable groups.

The term "ionisable functional group" as used herein refers to a group capable of forming ionic bonds, like an ammonium group, a carboxylate group or a guanidinium group.

Method and First Composition for Treating Hair

Hair proteins are the major structural components of the hair. The hair proteins are mostly composed of keratin and keratin associated proteins. The keratin and keratin associated proteins are comprised of specific arrangements of 21 amino acids. The amino acids comprise a large proportion of amino groups and carboxylic acid groups. Also, the keratin and keratin associated proteins contain a large proportion of the amino acid cysteine (circa 17%). Two cysteines can usually form a disulfur bond inside the hair.

The cuticle is the outer protective covering that covers the cortex of each human hair strand and is responsible for the luster and texture of human hair. The normal cuticle is smooth, allowing light reflection and limiting friction between the hair shafts. It's made up of six to eight layers of flattened overlapping cells and covered by an invisible, water-resistant lipid layer, which acts as a natural conditioner, namely the F-layer. This fatty acid layer (F-layer) is what naturally gives human hair its smooth and silky feel. Chemical processes such as coloring perming and relaxing strip the cuticle of the F-layer, which leads to what is generally referred to as "chemically-damaged" hair.

Due to perhydrolysis upon pre-treatment of the hair (Bleaching process), the F-layer is removed. The epicuticle then possesses on its surface a plurality of sulfonate groups (—SO$_3^-$). As a consequence, the interfiber friction increases, enhancing hair breakage.

Also, the disulfur bond between two cysteine amino acids can be broken upon reductive permanent hair waving. The resulting thiol groups of the cysteine can be oxidized into sulfonates during bleaching processes. As a result, the tensile strength of hair decreases, promoting readily hair breakage, but also the swelling increased, promoting a relatively faster wash-out of dyes.

The aminoacids of the hair proteins are linked to each other via peptide bonds. Peptide bonds are formed between the amino—and the carboxylic acid—groups of two aminoacids. Those peptide bonds can be broken as a result of reductive—as well as oxidative—chemical treatment of the hair, promoting hair breakage and reduced hair elasticity.

The present inventor has surprisingly found that when applying sequentially a first composition comprising one or more at least bi-functional carboxylic acids, or cosmetically acceptable salts thereof, and the first composition having a pH value of 7 to 13, and applying a second composition comprising one or more at least bi-functional carboxylic acids, or cosmetically acceptable salts thereof, and the second composition having a pH value of 3 to 7, hair elasticity can be significantly improved and breakage of the hair can be prevented.

The first composition can have a pH of at least 7, for example between 7.1 and 13. According to an embodiment, the pH of the first composition is from 7.5 to 12, particularly from 8.0 to 11, such as from 8.5 to 10, or from 9.0 to 10, or from 9.1 to 10, or from 9.2 to 10.

According to an embodiment, the first composition additionally include a pH modifier and/or buffering agent in an amount that is sufficiently effective to adjust the pH of the first composition.

The second composition can have a pH of less than 7, for example between 3.5 and 6.9. According to an embodiment, the second composition has a pH from 3.5 to 6.5, particularly from 3.5 to 5.5, such as from 3.7 to 5.0.

According to an embodiment, the second composition additionally include a pH modifier and/or buffering agent in an amount that is sufficiently effective to adjust the pH of the second composition.

Without wishing to be bound by theory, it is believed that the one or more at least bi-functional carboxylic acid of the first composition, having a pH value of 7 to 13, e.g. Sodium Malate effectively penetrates the hair and can cross-link the ammonium-groups of the hair. Unreacted amounts of the at least bi-functional carboxylic acid of the first composition which penetrate the hair more effectively at pH 7 to 13 compared to pH 3 to 7 due to more effective swelling of the hair at pH 7 to 13 may react in its acid form also with the amino-groups of the hair after the second composition as described herein was applied. Similarly, it is also assumed that the one or more at least bi-functional carboxylic acid of the second composition, having a pH value from 3 to 7, e.g. Malic Acid penetrates the hair and can cross-link the amino groups of the hair proteins by forming ionic bonds or hydrogen bonds. In addition, the low pH of the second composition will buffer the hair and the active agents provided with the first composition as described before. The effective amount of available amino- and ammonium-groups inside the hair is unknown. Hence, it is believed that any surplus of at least bi-functional carboxylic acid, or cosmetically acceptable salts thereof of the first and second composition have to be washed out after the treatment is completed.

Specific embodiments are related to methods for treating hair as stated hereinbefore. A method for treating hair according to an embodiment may include as a step (a), mixing a first composition with a hair treatment compositions, and as a step (b), applying to the hair the mixed composition. According to an embodiment, the first composition is mixed with water or an aqueous solution different to a hair treatment composition and then applied to the hair.

The first composition for treating hair may include, according to an embodiment, in a cosmetically acceptable carrier, one or more at least bi-functional carboxylic acids, or cosmetically acceptable salts thereof, or mixtures thereof, and may have a pH value from 7 to 13.

The one or more at least bi-functional carboxylic acid, or cosmetically acceptable salt thereof, may be a polyfunctional molecule which can optionally be independently substituted with one or more substituents which are selected from the group consisting of hydrogen, halogen, hydroxy, alkyl, alkenyl, alkynyl, alkoxy, cycloalkyl, cycloalkenyl, cycloalkynyl, aryl, heterocyclyl, heteroaryl, amine, formyl, acyl, carboxylic acid, —C(O)R$^1$, —C(O)OR$^1$, (—COO$^-$), —CONH$_2$, —CONHR$^1$, —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, —S(O)$_2$NR$^1$R$^2$, —SOR$^1$, or —SOOR$^1$ and mixtures thereof.

R$^1$ and R$^2$ each may be independently selected from the group consisting of a hydrogen, alkyl, alkenyl, alkynyl, cycloalkyl, cycloalkenyl, cycloalkynyl, aryl, heterocyclyl, and heteroaryl group. Each of R$^1$ and R$^2$ is independently unsubstituted or substituted with one or more substituents selected from the group consisting of halogen, hydroxy, alkyl, alkenyl, alkynyl, amino, alkylamino, dialkylamino, alkoxy, aryloxy, cycloalkyl, cycloalkenyl, cycloalkynyl, aryl, heterocyclyl, heteroaryl and mixtures thereof.

Hence, the one or more at least bi-functional carboxylic acid, or cosmetically acceptable salt thereof, can possess one or more substituents that is able to also form an ionic bond or a hydrogen bond with another group comprised in a typical damaged hair such as a sulfonate group or a thiolate group.

The one or more at least bi-functional carboxylic acid, or cosmetically acceptable salt thereof, may have a length from 2 to 12 carbon atoms, or from 2 to 6 carbon atoms. The one or more at least bi-functional carboxylic acid, or cosmetically acceptable salt thereof, can have a size, which can help to cross-link a plurality of amino acids of the hair proteins, typically by forming ionic bonds or hydrogen bonds.

According to an embodiment, the one or more at least bi-functional carboxylic acid, or cosmetically acceptable salt thereof, or mixtures thereof, may correspond to the following Formula 1:

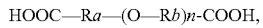

HOOC—R$a$—(O—R$b$)$n$-COOH, wherein Ra is selected from the group consisting of C1-C10 alkylene, C1-C10 cycloalkylene, C1-C10 alkenylene, C6-C12 (alkyl)arylene, Rb is C2-C4 alkylene, n is an integer from 0 to 4, wherein Ra and/or each Rb optionally are substituted with one or more substituents selected from —COOH, —OH, —NH2, —SH, and =O, and wherein the total number of carbon atoms in Ra plus Rb is 12 or less.

The one or more at least bi-functional carboxylic acid may be selected from the group consisting of Oxalic Acid, Malonic Acid, Succinic Acid, Glutaric Acid, Adipic Acid, Pimelic Acids, Suberic Acid, Azelaic Acid, Sebacic Acid, Maleic Acid, Fumaric Acid, Glutaconic Acid, Traumatic Acid, Muconic Acid, Glutinic Acid, Citracronic Acid, Mesaconic Acid, Malic Acid, Aspartic Acid, Glutamic Acid, Tartronic Acid, Tartaric Acid, Diaminopimelic Acid, Saccharic Acid, Mesoxalic Acid, Oxaloacetic Acid, Acetonedicarboxylic Acid, Arabinaric Acid, Phthalic Acid, Isophthalic Acid, Terephthalic Acid, Diphenic Acid, 2,6-Naphthalenedicarboxylic Acid, Citric Acid, Isocitric Acid, Aconitic Acid, Propane-1,2,3-tricarboxylic Acid, Trimesic Acid, Methanetetracarboxylic Acid, 1,2,3,4-Benzenetetracarboxylic Acid, 2,2'-(ethane-1,2-diylbis(azanediyl))disuccinic Acid, Aspergillomarasine Acid, Ethylenetetracarboxylic Acid, or derivatives thereof, or cosmetically acceptable salts thereof.

According to an embodiment, the one or more at least bi-functional carboxylic acid, or cosmetically acceptable salt thereof may be selected from the group consisting of saturated aliphatic carboxylic acids having two, three of four carboxylic acids groups, a total number of carbon atoms often or less, optionally substituted with one or more methyl and/or hydroxyl groups, or cosmetically acceptable salts thereof.

According to an embodiment, the one or more at least bi-functional carboxylic acid may be a saturated aliphatic at least bi-functional carboxylic acid. For example, the one or more at least bi-functional carboxylic acid may be selected from the group consisting of Malonic Acid, Succinic Acid, Glutaric Acid, Adipic Acid, Malic Acid, Tartaric Acid, Citric Acid, Isocitric Acid, Propane-1,2,3-tricarboxylic Acid, or cosmetically acceptable salts thereof, in particular malic acid or cosmetically acceptable salts thereof.

According to an embodiment, the at least bi-functional carboxylic acid is an at least bi-functional saturated carboxylic acid. Unsaturated carboxylic acid may not be sufficiently stable in a basic environment.

The first composition may have a pH from 7 to 14, or from 7 to 13, or from 7.5 to 13, or from 8 to 12, or from 8.1 to 11, or from 8.5 to 11, or from 8.5 to 10.5, or from 9.0 to 10.5, or from 9.1 to 10.5, or from 9.2 to 10.5. When the first composition has a pH from 7 to 14, the first composition is basic. Hence, the one or more at least bi-functional carboxylic acid, and derivatives thereof, may be present in the first composition as a cosmetically acceptable salt.

The first composition may comprise from 0.1% to 25%, or from 1% to 18%, or from 3% to 15%, or from 7.5% to 12%, or from 3% to 9% of the one or more at least bi-functional carboxylic acid, derivatives and cosmetically acceptable salts thereof by total weight of the first composition.

The method for treating hair may optionally further include as a step (c), applying to the hair a second composition comprising in a cosmetically acceptable carrier, one or more of the same or a different at least bi-functional carboxylic acid, derivative and cosmetically acceptable salt thereof, as described for step (a). The second composition may have a pH value of 3 to 7.

Thus, the one or more at least bi-functional carboxylic acid, or cosmetically acceptable salt thereof, may be a polyfunctional molecule which is independently substituted with one or more substituents which are selected from the group consisting of hydrogen, halogen, hydroxy, alkyl, alkenyl, alkynyl, alkoxy, cycloalkyl, cycloalkenyl, cycloalkynyl, aryl, heterocyclyl, heteroaryl, amine, formyl, acyl, carboxylic acid, —C(O)R$^1$, —C(O)OR$^1$, (—COO$^-$), —CONH$_2$, —CONHR$^1$, —C(O)NR$^1$R$^2$, —NR$^1$R$^2$, —NR$^1$S(O)$_2$R$^2$, —NR$^1$C(O)R$^2$, —S(O)$_2$R$^2$, —SR$^1$, —S(O)$_2$NR$^1$R$^2$, —SOR$^1$, or —SOOR$^1$ and mixtures thereof.

R$^1$ and R$^2$ each may be independently selected from the group consisting of a hydrogen, alkyl, alkenyl, alkynyl, cycloalkyl, cycloalkenyl, cycloalkynyl, aryl, heterocyclyl, and heteroaryl group. Each of R$^1$ and R$^2$ is independently unsubstituted or substituted with one or more substituents selected from the group consisting of halogen, hydroxy, alkyl, alkenyl, alkynyl, amino, alkylamino, dialkylamino, alkoxy, aryloxy, cycloalkyl, cycloalkenyl, cycloalkynyl, aryl, heterocyclyl, heteroaryl and mixtures thereof.

Hence, the one or more at least bi-functional carboxylic acid, or cosmetically acceptable salt thereof, can possess one or more substituents that is able to also form an ionic bond or a hydrogen bond with another group comprised in a typical damaged hair such as a sulfonate group or a thiolate group.

The one or more at least bi-functional carboxylic acids, or cosmetically acceptable salts thereof, may have a length from 2 to 12 carbon atoms, or from 2 to 6 carbon atoms. The one or more at least bi-functional carboxylic acid, or cosmetically acceptable salt thereof, can have a size, which can help to cross-link a plurality of amino acids of the hair proteins, particularly by forming ionic bonds or hydrogen bonds.

The one or more at least bi-functional carboxylic acid of the second composition may also be selected from the group consisting of Oxalic Acid, Malonic Acid, Succinic Acid, Glutaric Acid, Adipic Acid, Pimelic Acids, Suberic Acid, Azelaic Acid, Sebacic Acid, Maleic Acid, Fumaric Acid, Glutaconic Acid, Traumatic Acid, Muconic Acid, Glutinic Acid, Citracronic Acid, Mesaconic Acid, Malic Acid, Aspartic Acid, Glutamic Acid, Tartronic Acid, Tartaric Acid, Diaminopimelic Acid, Saccharic Acid, Mesoxalic Acid, Oxaloacetic Acid, Acetonedicarboxylic Acid, Arabinaric Acid, Phthalic Acid, Isophthalic Acid, Terephthalic Acid, Diphenic Acid, 2,6-Naphthalenedicarboxylic Acid, Citric Acid, Isocitric Acid, Aconitic Acid, Propane-1,2,3-tricarboxylic Acid, Trimesic Acid, Methanetetracarboxylic Acid, 1,2,3,4-Benzenetetracarboxylic Acid, 2,2'-(ethane-1,2-diyl-bis(azanediyl))disuccinic Acid, Aspergillomarasine Acid, Ethylenetetracarboxylic Acid, or derivatives thereof, or cosmetically acceptable salts thereof.

The second composition may have a pH from 3 to 7, or from 3.5 to 6.5, or from 3.5 to 6.5 or from 3.7 to 5.0. When the second composition has a pH from 3 to 7, the second composition is acidic. Depending on its pKs values, the one or more at least bi-functional carboxylic acid, and derivatives thereof, will be present protonated or at least partially deprotonated.

The second composition may comprise from 0.01% to 25%, or from 0.5% to 15%, or from 1.0% to 10%, or from 1.5% to 5.0%, or from 1.5% to 3.0% of the one or more at least bi-functional carboxylic acid, derivatives and cosmetically acceptable salts thereof by total weight of the second composition.

The step (b) of the method may typically occur prior to step (c). Alternatively, step (c) of the method may occur prior to step (b).

The method may optionally further include as a step (d), the step of rinsing, shampooing, conditioning the hair, or a combination thereof. The step (d) may occur subsequent to step (b) and/or step (c). The first composition can be optionally mixed with commercially available hair coloring, hair bleaching, or permanent hair waving compositions, which is referred to as hair treatment composition, followed by step (c) of the method, optionally followed by step (d). Alternatively, the method can occur as part of a hair coloring, or hair bleaching, or permanent hair waving procedure such that the first formulation is applied either after a hair coloring, a hair bleaching, or a permanent hair waving composition is applied, followed by step (c) of the method, optionally followed by step (d) of the method.

The method may further comprise a step (e), the step of drying the hair. Without wanting to be bound by theory it is believed that hair drying after steps (b) and (c) can lead to covalent bonds being created between the formula ingredients of the first and the second composition and the functional groups of the hair proteins. Suitable devices for carrying out step (e) comprise hair dryers, hair straighteners, curling irons, or hoods. Step (e) can occur after step (c) or step (d) of the method.

pH

The first composition may have a pH from 7 to 14, or from 7.1 to 13, or from 7.5 to 13, or from 8 to 12, or from 8.1 to 11, or from 8.5 to 11, or from 8.5 to 10.5, or from 9.0 to 10.5, or from 9.1 to 10.5, or from 9.2 to 10.5. The second composition may have a pH from 3 to 7, or from 3.5 to 6, or from 4 to 5.

According to an embodiment, the first composition and/or the second composition may comprise a pH modifier and/or buffering agent in an amount that is sufficiently effective to adjust the pH of the first composition and/or the second composition to fall within a range prescribed above. Suitable pH modifiers and/or buffering agents for use herein may include, but are not limited to ammonia, alkanolamines such as monoethanolamine, diethanolamine, triethanolamine, monopropanolamine, dipropanolamine, tripropanolamine, 2-amino-2-methyl-1-propanol, and 2-amino-2-hydroxymethyl-1,3,-propandiol and guanidium salts, alkali metal or ammonium hydroxides and carbonates.

Suitable pH modifiers and/or buffering agents may particularly include sodium hydroxide, sodium silicate, sodium meta silicate and ammonium carbonate, and acidulents such as organic and inorganic acids, e.g., phosphoric acid, acetic acid, ascorbic acid, citric acid or tartaric acid, hydrochloric acid, and mixtures thereof.

According to an embodiment, the hair treatment composition has a pH higher than 7. When mixing the hair treatment composition with the first composition, the pH of the hair treatment composition is not significantly changed so that the desired pH of the hair treatment composition is maintained in the mixed composition. For example, the difference between the pH of the first composition and the hair treatment composition may be 2 or less, particularly 1.5 or less, more particularly 1.2 or less, such as 1.0 or less. Further, the difference between the pH of the hair treatment composition and the pH of the mixed composition may be 0.5 or less. For example, the difference between the pH of the hair treatment composition and the pH of the mixed composition may be 0.5 or less, particularly 0.3 or less, more particularly 0.2 or less, such as 0.15 or less.

In the context of a coloring composition as a hair treatment composition, the term "pH of the hair treatment composition" denotes the pH of a (ready-to-use prior art) coloring composition prepared by mixing commercially available developer and cream color in the amounts required for the intended use. In the context of a bleaching composition as a hair treatment composition, the term "pH of the hair treatment composition" denotes the pH of a (ready-to-use prior art) bleaching composition prepared by mixing commercially available bleach powder and hydrogen peroxide solution in the amounts required for the intended use. In the context of a permanent hair waving composition as a hair treatment composition, the term "pH of the hair treatment composition" denotes the pH of a commercially available reducing solution such as a thioglycolic acid or thioglycolate solution.

According to an embodiment, the pH of the first composition is higher than the pH of the hair treatment composition. According to an embodiment, the pH of the first composition is lower than the pH of the hair treatment composition.

When maintaining the desired pH of the hair treatment composition in the mixed composition, or when limiting the change of the pH when mixing the first composition and the hair treatment composition to a certain amount, the efficacy of the hair treatment composition is preserved. This is beneficial in comparison to approaches where an acidic composition is mixed with a hair treatment composition which significantly changes the pH of the mixed composition. The efficacy of those mixed compositions is reduced. An example is hair coloring with oxidative coloring agents. A reduction of the pH impairs the coloring efficacy. As a consequence, the amount of the dye precursors is commonly increased to compensate the reduced efficacy, or the application time is commonly increased to compensate the reduced efficacy. Another example is bleaching. To compensate the reduced bleaching efficacy due to pH lowering, the amount of bleaching agent is commonly increased leading to an even higher damaging of the hair, or the application time is increased. Both commonly used countermeasures are unpleasant for the customer and may even increase hair damage.

Using a first composition having a high, or basic, pH as described herein in embodiments, a change or reduction of the pH can be avoided or at least substantially reduced. The above described beneficial effects of the at least bi-functional carboxylic acid can thus be obtained without significantly impairing the intended coloring, bleaching or permanent waving or straightening of the hair unlike other approaches. Furthermore, a prolonged application of the mixed composition is not needed which improves customer's comfort.

Oxidizing Agents

The hair treatment composition and thus the mixed composition may comprise one or more oxidizing agents. The term "oxidizing agent" is used herein interchangeable with the term "bleaching agent". Alternatively, or additionally, the second composition may comprise one or more oxidizing agents. Typical oxidizing agents are water-soluble peroxygen oxidizing agents. The one or more oxidizing agents can be valuable for the initial solubilisation and decolorisation of the melanin (bleaching) and accelerate the oxidation of the oxidative dye precursors (oxidative dyeing) in the hair shaft.

The one or more oxidizing agents may be present in an amount sufficient to bleach melanin pigment in hair and/or cause formation of dye chromophores from oxidative dye precursors. Typically, the hair treatment composition, the mixed composition and/or the second composition may comprise a total amount of oxidizing agents ranging from 0.1% to 20%, or from 0.5% to 12%, or from 1% to 10%, or from 2% to 5%, by total weight of the respective first composition and/or the second composition.

Suitable water-soluble oxidizing agents may include, but are not limited to: inorganic peroxygen materials capable of yielding hydrogen peroxide in an aqueous solution.

Suitable water-soluble peroxygen oxidizing agents may include, but are not limited to: hydrogen peroxide; inorganic alkali metal peroxides (such as sodium periodate and sodium peroxide); organic peroxides (such as urea peroxide and melamine peroxide); inorganic perhydrate salt bleaching compounds (such as the alkali metal salts of perborates, percarbonates, perphosphates, persilicates, persulphates and the like); and mixtures thereof. Inorganic perhydrate salts may be incorporated for example as monohydrates, tetrahydrates. Alkyl/aryl peroxides and/or peroxidases may also be used. Mixtures of two or more such oxidizing agents can be used if desired. The oxidizing agents may be provided in aqueous solution or as a powder which is dissolved prior to use.

The hair treatment composition, the mixed composition, and/or the second composition may particularly comprise a water-soluble oxidizing agent which is selected from the group consisting of hydrogen peroxide, percarbonates (which may be used to provide a source of both oxidizing agent and carbonate ions), persulphates, and mixtures thereof. The one or more oxidizing agents of the hair treatment composition, the mixed composition, and/or the second composition may be sodium percarbonate. The first composition, the hair treatment composition, the mixed composition, and/or the second composition may be substantially free of persulfate.

According to an embodiment, the first composition is substantially free of, or is free of, oxidizing agents.

Oxidative Dye Precursors

The hair treatment composition and the mixed composition may comprise oxidative dyes precursors comprising one or more couplers (also known as secondary intermediate) and one or more primary intermediates (also known as developer). Alternatively, or additionally, the second composition may comprise oxidative dyes precursors comprising one or more couplers and one or more primary intermediates. Various couplers may be used with primary intermediates in order to obtain different shades.

The oxidative dye precursors suitable for use herein, in so far as they are bases, may be used as free bases or in the form of any cosmetically acceptable salts obtained with the corresponding organic or inorganic acids, such as hydrochloric, hydrobromic, citric, acetic, lactic, succinic, tartaric, or sulfuric acids, or, in so far as they have aromatic hydroxyl groups, in the form of any cosmetically acceptable salts obtained with the corresponding bases, such as alkali phenolates.

Oxidative dye precursors are known in the art, and include aromatic diamines, aminophenols, aromatic diols and their derivatives (a representative but not exhaustive list of oxidation dye precursors can be found in Sagarin, "Cosmetic Science and Technology, Interscience, Special Edn. Vol. 2 pages 308 to 310). Suitable oxidative dye precursors are also disclosed in the Canadian Patent Application No. CA 2 576 189 A1—in particular, from Table 1 dye combinations No. 1 to 2394, which span pages 49 to 238, are incorporated herein by reference. It is to be understood that the one or more primary intermediates and the one or more couplers (collectively known as oxidative dye precursors) detailed below are only by way of example and are not intended to limit the first composition and/or the second composition and other aspects herein described. The one or more primary intermediates and the one or more couplers may be used in the form of any cosmetically acceptable salts, for example sulfate salts.

The one or more primary intermediates of the hair treatment composition, the mixed composition and/or the second composition may be selected from the group consisting of toluene-2,5-diamine, p-phenylenediamine, N-phenyl-p-phenylenediamine, N,N-bis(2-hydroxyethyl)-p-phenylenediamine, 2-hydroxyethyl-p-phenylenediamine, hydroxypropyl-bis-(N-hydroxyethyl-p-phenylenediamine), 2-methoxymethyl-p-phenylenediamine, 2-(1,2-dihydroxyethyl)-p-phenylenediamine, 2,2'-(2-(4-aminophenylamino) ethylazanediyl)diethanol, 2-(2,5-diamino-4-methoxyphenyl)propane-1,3-diol, 2-(7-amino-2H-benzo[b][1,4]oxazin-4(3H)-yl)ethanol, 2-chloro-p-phenylenediamine, p-aminophenol, p-(methylamino)phenol, 4-amino-m-cresol, 6-amino-m-cresol, 5-ethyl-o-aminophenol, 2-methoxy-p-phenylenediamine, 2,2'-methylenebis-4-aminophenol, 2,4,5, 6-tetraminopyrimidine, 2,5,6-triamino-4-pyrimidinol, 1-hydroxyethyl-4,5-diaminopyrazole sulfate, 4,5-diamino-1-methylpyrazole, 4,5-diamino-1-ethylpyrazole, 4,5-diamino-1-isopropylpyrazole, 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1(5H)-one dimethosulfonate, 4,5-diamino-1-hexylpyrazole, 4,5-diamino-1-heptylpyrazole, methoxymethyl-1,4-diaminobenzene, N,N-bis(2-hydroxyethyl)-N-(4-aminophenyl)-1,2-diaminothane, 2-[(3-aminopyrazolo[1,5-a]pyridin-2-yl)oxy]ethanol hydrochloride, salts thereof and mixtures thereof.

The one or more primary intermediate of the hair treatment composition, the mixed composition and/or the second composition may be particularly 1,4-diamino-2-(methoxymethyl)-benzene. 1,4-diamino-2-(methoxymethyl)-benzene has the advantage of an improved sensitisation profile (i.e. reduced risks of scalp skin reaction).

The one or more primary intermediate may be 4,5-diamino-1-hexylpyrazole. 4,5-diamino-1-hexylpyrazole may be used as a sulfate salt.

The one or more primary intermediate may be selected from the group consisting of 4,5-diamino-1-butylpyrazole, 4,5-diamino-1-pentylpyrazole, 4,5-diamino-1-benzylpyrazole, 2,3-diamino-6,7-dihydropyrazolo[1,2-a]pyrazol-1 (5H)-one dimethosulfonate, 4,5-diamino-1-hexylpyrazole, 4,5-diamino-1-heptylpyrazole, methoxymethyl-1,4-diaminobenzene, and mixtures thereof; and the cosmetically acceptable salts thereof such as chlorides, sulfates and hemi-sulfates in particular.

The one or more couplers may be a compound comprising at least one phenyl ring substituted with at least one hydroxyl group. The one or more couplers may be selected from the group consisting of resorcinol, 4-chlororesorcinol, 2-chlororesorcinol, 2-methylresorcinol, 4,6-dichlorobenzene-1,3-diol, 2,4-dimethylbenzene-1,3-diol, m-aminophenol, 4-amino-2-hydroxytoluene, 2-methyl-5-hydroxyethylaminophenol, 3-amino-2,6-dimethylphenol, 3-amino-2,4-dichlorophenol, 5-amino-6-chloro-o-cresol, 5-amino-4-chloro-o-cresol, 6-hydroxybenzomorpholine, 2-amino-5-ethylphenol, 2-amino-5-phenylphenol, 2-amino-5-methylphenol, 2-amino-6-methylphenol, 2-amino-5-ethoxyphenol, 5-methyl-2-(methylamino)phenol, 2,4-diaminophenoxyethanol, 2-amino-4-hydroxyethylaminoanisole, 1,3-bis-(2,4-diaminophenoxy)-propane, 2,2'-(2-methyl-1,3-phenylene)bis(azanediyl) diethanol, benzene-1,3-diamine, 2,2'-(4,6-diamino-1,3-phenylene)bis(oxy)diethanol, 3-(pyrrolidin-1-yl)aniline, 1-(3-(dimethylamino)phenyl)urea, 1-(3-aminophenyl)urea, 1-naphthol, 2-methyl-1-naphthol, 1,5-naphthalenediol, 2,7-naphthalenediol, 1-acetoxy-2-methylnaphthalene, 4-chloro-2-methylnaphthalen-1-ol, 4-methoxy-2-methylnaphthalen-1-ol, 2,6-dihydroxy-3,4-dimethylpyridine, 2,6-dimethoxy-3, 5-pyridinediamine, 3-amino-2-methylamino-6-methoxypyridine, 2-amino-3-hydroxypyridine, 2,6-diaminopyridine, pyridine-2,6-diol, 5,6-dihydroxyindole, 6-hydroxyindole, 5,6-dihydroxyindoline, 3-methyl-1-phenyl-1H-pyrazol-5(4H)-one, 1,2,4-trihydroxybenzene, 2-(benzo[d][1,3]dioxol-5-ylamino)ethanol (also known as hydroxyethyl-3,4-methylenedioxyaniline), and mixtures thereof.

The oxidative dye precursors may be particularly selected from the group consisting of 1-naphthol, 2,4-diaminophenoxyethanol, toluene-2,5-diamine sulfate, resorcinol, 4-amino-m-cresol, 2-amino-6-chloro-4-nitrophenol, 2-amino-4-hydroxyethylaminoanisole sulfate, hydroxyethyl-3,4-methylenedioxyaniline HCl, 1-hydroxyethyl 4,5-diamino pyrazole sulfate, 4-amino-2-hydroxytoluene, 2-methylresorcinol, m-aminophenol, 2-methyl-5-hydroxyethylaminophenol, and mixtures thereof.

The oxidative dye precursors may comprise particularly 5-amino-4-chloro-o-cresol and 1,4-diamino-2-(methoxymethyl)-benzene. The oxidative dye precursors may comprise more particularly 2,6-diaminopyridine and 1,4-diamino-2-(methoxymethyl)-benzene. The oxidative dye precursors may comprise even more particularly 2,6-dihydroxyethylaminotoluene and 2-methoxymethyl-1,4-diaminobenzene. The oxidative dye precursors may comprise even more particularly 2-methoxymethyl-1,4-diaminobenzene and p-phenylenediamine and/or toluene-2,5-diamine.

Typically, the hair treatment composition, the mixed composition and/or the second composition may comprise a total amount of oxidative dye precursors, namely the one or more couplers and the one or more primary intermediates, up to 12%, or from 0.001% to 12%, or from 0.01% to 10%, or from 0.3% to 8%, or from 0.05% to 9%, or from 0.5% to 6% of oxidative dye precursors by total weight of the respective composition.

The first composition, the hair treatment composition, the mixed composition and/or the second composition may be substantially free of oxidizing agent.

According to an embodiment, the first composition is substantially free of, or is free of, oxidative dye precursors.
Direct Dye The hair treatment composition, the mixed composition and/or the second composition may further comprise one or more direct dyes, advantageously one or more oxidatively stable direct dyes.

The hair treatment composition, the mixed composition, and/or the second composition may comprise a total amount from 0.001% to 4%, or from 0.005% to 3%, or from 0.01% to 2% of the one or more direct dyes by total weight of the respective composition.

The presence of one or more direct dyes and the proportion thereof can help to provide or enhance coloring/dyeing, particularly with regard to the vibrancy of the color that is desired.

The first composition and/or the second composition may be substantially free of any direct dyes. Indeed, sometimes consumers prefer direct dye-free compositions.

The one or more direct dyes may be selected from the group consisting of nitro dyes to provide a blue color, nitro dyes to provide wither a red color or a yellow color, quinone dyes, basic dyes, neutral azo dyes, acid dyes, and mixtures thereof. The one or more direct dyes may be a basic dye. The one or more direct dyes may be a neutral azo dye. The one or more direct dyes may be an acid dye.

The one or more direct dyes may be selected from the group consisting of Acid dyes such as Acid Yellow 1, Acid Orange 3, Acid Black 1, Acid Black 52, Acid Orange 7, Acid Red 33, Acid Yellow 23, Acid Blue 9, Acid Violet 43, Acid Blue 16, Acid Blue 62, Acid Blue 25, Acid Red 4, Basic Dyes such as Basic Brown 17, Basic Red 118, Basic Orange 69, Basic Red 76, Basic Brown 16, Basic Yellow 57, Basic Violet 14, Basic Blue 7, Basic Blue 26, Basic Red 2, Basic Blue 99, Basic Yellow 29, Basic Red 51, Basic Orange 31, Basic Yellow 87, Basic Blue 124, 4-(3-(4-amino-9,10-di-oxo-9,10-dihydroanthracen-1-ylamino)propyl)-4-methyl-morpholin-4-ium-methylsulfate, (E)-1-(2-(4-(4,5-dimethyl-thiazol-2-yl)diazenyl)phenyl)(ethyl)amino)ethyl)-3-methyl-1H-imidazol-3-ium chloride, (E)-4-(2-(4-(dimethylamino) phenyl)diazenyl)-1-methyl-1H-imidazol-3-ium-3-yl) butane-1-sulfonate, (E)-4-(4-(2-methyl-2-phenylhydrazono) methyl)pyridinium-1-yl)butane-1-sulfonate, N,N-dimethyl-3-(4-(methylamino)-9,10-dioxo-4a,9,9a,10-tetrahydroanthracen-1-ylamino)-N-propylpropan-1-aminium bromide, Disperse Dyes such as Disperse Red 17, Disperse Violet 1, Disperse Red 15, Disperse Black 9, Disperse Blue 3, Disperse Blue 23, Disperse Blue 377, Nitro Dyes such as 1-(2-(4-nitrophenylamino)ethyl)urea, 2-(4-methyl-2-nitrophenylamino)ethanol, 4-nitrobenzene-1,2-di-amine, 2-nitrobenzene-1,4-diamine, Picramic acid, HC Red No. 13, 2,2'-(2-nitro-1,4-phenylene)bis(azanediyl)diethanol, HC Yellow No. 5, HC Red No. 7, HC Blue No. 2, HC Yellow No. 4, HC Yellow No. 2, HC Orange No. 1, HC Red No. 1, 2-(4-amino-2-chloro-5-nitrophenylamino)ethanol, HC Red No. 3, 4-amino-3-nitrophenol, 4-(2-hydroxyethylamino)-3-nitrophenol, 2-amino-3-nitrophenol, 2-(3-(methylamino)-4-nitrophenoxy)ethanol, 3-(3-amino-4-nitrophenyl)propane-1,2-diol, HC Yellow No. 11, HC Violet No. 1, HC Orange No. 2, HC Orange No. 3, HC Yellow No. 9, HC Red No. 10, HC Red No. 11, 2-(2-hydroxyethylamino)-4,6-dinitrophenol, HC Blue No. 12, HC Yellow No. 6, HC Yellow No. 12, HC Blue No. 10, HC Yellow No. 7, HC Yellow No. 10, HC Blue No. 9, 2-chloro-6-(ethylamino)-4-nitrophenol, 6-nitropyridine-2,5-diamine, HC Violet No. 2, 2-amino-6-chloro-4-nitrophenol, 4-(3-hydroxypropylamino)-3-nitrophenol, HC Yellow No. 13, 6-nitro-1,2,3,4-tetrahydroquinoxaline, HC Red No. 14, HC Yellow No. 15, HC Yellow No. 14, N2-methyl-6-nitropyridine-2,5-diamine, N1-allyl-2-ni-trobenzene-1,4-diamine, HC Red No. 8, HC Green No. 1, HC Blue No. 14, and Natural dyes such as Annato, Anthocyanin, Beetroot, Carotene, Capsanthin, Lycopene, Chlorophyll, Henna, Indigo, Cochineal, and mixtures thereof.

According to an embodiment, the first composition is substantially free of, or is free of, direct dyes.

Other Ingredients

The first composition, the hair treatment composition, the mixed composition, and/or the second composition according to embodiments may comprise, in addition to the ingredients indicated above, further ingredients in order to further enhance the properties of the first composition and/or the second composition, as long as these are not excluded by the claims.

Suitable further ingredients may include, but not limited to: pigments, coloured material, solvents, radical scavengers, peroxymonocarbonate ions, surfactants, thickening agents, conditioning agents (such as silicones and cationic polymers), cosmetically acceptable carrier, preservatives, perfume and mixtures thereof.

Suitable further ingredients referred to above, but not specifically described below, are listed in the International Cosmetics Ingredient Dictionary and Handbook, (8th ed.; The Cosmetics, Toiletry, and Fragrance Association). Particularly, vol. 2, sections 3 (Chemical Classes) and 4 (Functions), which are useful in identifying specific adjuvants to achieve a particular purpose or multipurpose. A few of these ingredients are discussed hereinbelow, whose disclosure is of course non-exhaustive.

Pigment

The first composition, the hair treatment composition, the mixed composition, and/or the second composition may comprise one or more pigments. The one or more pigments of the first composition, the hair treatment composition, the mixed composition, and/or the second composition may be a colored pigment which imparts color effects to the first composition, the hair treatment composition, the mixed composition, and/or the second composition or to the hair.

Alternatively, the one or more pigments of the first composition, the hair treatment composition, the mixed composition, and/or the second composition may be a luster effect pigment which imparts desirable and aesthetically pleasing luster effects to the first composition and/or the second composition or to the keratin fibers of the hair. The color or luster effects on the keratin fibers of the hair are particularly temporary. Indeed, the color or luster effects on the keratin fibers of the hair last until the next hair wash and can be removed again by washing the hair with customary shampoos.

The first composition and/or the second composition may be substantially free of pigment. Indeed, having the first composition and/or the second composition substantially free of pigment can help to prevent the formation of residues, precipitation and/or rough hair feel.

The first composition, the hair treatment composition, the mixed composition, and/or the second composition may comprise one or more pigments having a $D_{50}$ particle diameter of from 5 μm to 60 μm measured according to the following test method. Particle diameter is represented by $D_{50}$, which is the median diameter by volume. $D_{50}$ is measured with a Malvern Mastersizer 2000, which is a laser diffraction particle sizer and it is measured according to ISO 13320:2009(en) with Hydro 2000G or Hydro 2000S where the dispersant is water or ethanol. Detection range is from 0.02 μm to 2000 μm. $D_{50}$ is expressed as $x_{50}$ in ISO 13320:2009(en). Laser diffraction measures particle size distributions by measuring an angular variation in intensity of light scattered as a laser beam passes through a dispersed particulate sample analyzer and the particle size is reported as a volume equivalent sphere diameter. A discussion of calculating $D_{50}$ is provided in Barber et al, Pharmaceutical Development and Technology, 3(2), 153-161 (1998), which is incorporated herein by reference.

The first composition, the hair treatment composition, the mixed composition, and/or the second composition may comprise a pigment having a $D_{50}$ particle diameter from 10 μm to 40 μm. The one or more pigments of the first composition, the hair treatment composition, the mixed composition, and/or the second composition may be present in the first composition, the hair treatment composition, the mixed composition, and/or the second composition in an undissolved form. The first composition, the hair treatment composition, the mixed composition, and/or the second composition may comprise from 0.01% to 25%, or from 0.1% to 20%, or from 1% to 15%, or from 4% to 10% of the one or more pigments by total weight of the respective composition.

The one or more pigments of the first composition, the hair treatment composition, the mixed composition, and/or the second composition may be a colorant which is virtually insoluble in the first composition, the hair treatment composition, the mixed composition, and/or the second composition, and may be inorganic or organic. Inorganic-organic mixed pigments may be also possible. The first composition, the hair treatment composition, the mixed composition, and/or the second composition may comprise an inorganic pigment. The advantage of an inorganic pigment is its excellent resistance to light, weather and temperature. The inorganic pigment of the first composition, the hair treatment composition, the mixed composition, and/or the second composition may be of natural origin, and may be, for example, derived from a material selected from the group consisting of chalk, ochre, umber, green earth, burnt sienna, and graphite.

The one or more pigments of the first composition, the hair treatment composition, the mixed composition, and/or the second composition may be a white pigment, such as, for example, titanium dioxide or zinc oxide. Alternatively, the one or more pigments of the first composition, the hair treatment composition, the mixed composition, and/or the second composition may be a black pigment, such as, for example, iron oxide black. Alternatively, the one or more pigments of the first composition, the hair treatment composition, the mixed composition, and/or the second composition may be a colored pigment, such as, for example, ultra-marine or iron oxide red, or a luster pigment, or a metal effect pigment, or a pearlescent pigment, and/or a fluorescent or phosphorescent pigment.

The one or more pigments of the first composition, the hair treatment composition, the mixed composition, and/or the second composition may be colored or a non-white pigment. The one or more pigments of the first composition, the hair treatment composition, the mixed composition, and/or the second composition may be selected from the group consisting of metal oxides, hydroxides and oxide hydrates, mixed phase pigments, sulfur-containing silicates, metal sulfides, complex metal cyanides, metal sulfates, chromates and molybdates, the metals themselves (bronze pigments), and combinations thereof. The one or more pigments of the first composition, the hair treatment composition, the mixed composition, and/or the second composition may be selected from the group consisting of are titanium dioxide (CI 77891), black iron oxide (CI 77499), yellow iron oxide (CI 77492), red and brown iron oxide (CI 77491), manganese violet (CI 77742), ultramarine (sodium aluminium sulfosilicates, CI 77007, Pigment Blue 29), chromium oxide hydrate (CI 77289), Prussian blue (ferric ferrocyanide, CI 77510), carmine (cochineal), and combinations thereof.

The one or more pigments of the first composition, the hair treatment composition, the mixed composition, and/or the second composition may be a pearlescent and colored pigment based on mica which is coated with a metal oxide or a metal oxychloride, such as titanium dioxide or bismuth oxychloride, and optionally further color-imparting substances, such as iron oxides, Prussian blue, ultramarine, and carmine. The color exhibited by the pigment may be adjusted by varying the layer thickness. Such pigments are sold, for example, under the trade names Rona®, Colorona®, Dichrona®, RonaFlair®, Ronastar®, Xirona® and Timiron® all of which are available from Merck, Darmstadt, Germany. For example, Xirona® is a brand for color travel pigments that display color shifting effects depending on the viewing angle and are based on either natural mica, silica or calcium aluminium borosilicate flakes, coated with varying layers of titanium dioxide.

Pigments from the line KTZ® from Kobo Products, Inc., 3474 So. Clinton Ave., So. Plainfield, USA, may be also useful herein, in particular the Surface Treated KTZ® Pearlescent Pigments from Kobo. Particularly useful are KTZ® FINE WHITE (mica and $TiO_2$) having a $D_{50}$ particle diameter from 5 μm to 25 μm and also KTZ® CELESTIAL LUSTER (mica and $TiO_2$, from 10 μm to 60 μm) as well as KTZ® CLASSIC WHITE (mica and $TiO_2$, from 10 μm to 60 μm). Another useful pigment may be SynCrystal Sapphire from Eckart Effect Pigments, which is a blue powder comprising platelets of synthetic fluorphlogopite coated with titanium dioxide, ferric ferrocyanide and small amounts of tin oxide. Another useful pigment may also be SYNCRYSTAL Almond also from Eckart, which is a beige powder with a copper reflection color and is composed of platelets of synthetic fluorphlogopite and coated with titanium dioxide and iron oxides. Another useful pigment may be Duocrome® RV 524C from BASF, which provides a two color look via a lustrous red powder with a violet reflection powder due to its composition of mica, titanium dioxide and carmine.

The one or more pigments of the first composition, the hair treatment composition, the mixed composition, and/or the second composition may be an organic pigment. The organic pigment of the first composition, the hair treatment composition, the mixed composition, and/or the second composition may be selected from the group consisting of natural pigments sepia, gamboge, bone charcoal, Cassel brown, indigo, chlorophyll and other plant pigments.

The one or more pigments of the first composition, the hair treatment composition, the mixed composition, and/or the second composition may be a synthetic organic pigment. The synthetic organic pigment of the first composition and/or the second composition may be selected from the group consisting of azo pigments, anthraquinoids, indigoids, dioxazine, quinacridone, phthalocyanine, isoindolinone, perylene and perinone, metal complex, alkali blue, diketopyrrolopyrrole pigments, and combinations thereof.

The one or more pigments of the first composition, the hair treatment composition, the mixed composition, and/or the second composition may be selected from the group consisting of iron oxide, titanium dioxide, mica, borosilicate, and combinations thereof. The pigment of the first composition and/or the second composition may comprise an iron oxide ($Fe_2O_3$) pigment. The one or more pigments of the first composition, the hair treatment composition, the mixed composition, and/or the second composition may comprise a combination of mica and titanium dioxide.

Colored Material

The first composition, the hair treatment composition, the mixed composition, and/or the second composition may comprise one or more colored materials. The one or more colored materials of the first composition, the hair treatment composition, the mixed composition, and/or the second composition may be particulate in form. The one or more colored materials of the first composition, the hair treatment composition, the mixed composition, and/or the second composition may be selected from the group consisting of colored fibers, colored beads, colored particles such as nano-particles, colored polymers comprising covalently attached dyes, liquid crystals, particles having diffraction properties, UV absorber and photoprotective substances, pressure- or light-sensitive pigments, and combinations thereof.

The first composition, the hair treatment composition, the mixed composition, and/or the second composition may be substantially free of colored material. Indeed, having the first composition, the hair treatment composition, the mixed composition, and/or the second composition substantially free of colored material can help to prevent the formation residues and precipitation.

The one or more colored materials of the first composition, the hair treatment composition, the mixed composition, and/or the second composition may be capable of changing color via a mechanism selected from the group consisting of thermochromism, photochromism, hydrochromism, magnetochromism, electrochromism, piezochromism, chemichromism, mechano-optics. Suitable colored material of the first composition and/or the second composition may include 3D Magnetic Pigments, Glow Dust, Fluorescent Pigments, Thermo Dust, Chameleon Pigments and other color changing materials from Solar Color Dust (http://solarcolordust.com/).

The first composition, the hair treatment composition, the mixed composition, and/or the second composition may comprise one or more photoprotective substances. The first composition, the hair treatment composition, the mixed composition, and/or the second composition may comprise from 0.01% to 10%, or from 0.1% to 5%, or from 0.2% to 2% of the one or more photoprotective substances by total weight of the respective composition. Useful photoprotective substances of the first composition, the hair treatment composition, the mixed composition, and/or the second composition are specified in European Patent Application EP 1 084 696 A1 from § 0036 to § 0053, which is incorporated herein by reference. The one or more photoprotective substances of the first composition, the hair treatment composition, the mixed composition, and/or the second composition may be selected from the group consisting of 2-ethylhexyl 4-methoxycinnamate, methyl methoxycinnammate, 2-hydroxy-4-methoxybenzophenone-5-sulfonic acid, polyethoxylated p-aminobenzoates, di-butyl-hydroxytoluene (BHT), and mixtures thereof.

The first composition, the hair treatment composition, the mixed composition, and/or the second composition may comprise from 0.01% to 10%, or from 0.05% to 5% of one or more particulate substances by total weight of the respective composition. The one or more particulate substances of the first composition and/or the second composition may be a substance which is solid at room temperature (23° C.) and in the form of a particle. The one or more particulate substances of the first composition, the hair treatment composition, the mixed composition, and/or the second composition may be selected from the group consisting of silica, silicates, aluminates, clay earths, mica, and insoluble salts. The one or more particulate substances of the first composition, the hair treatment composition, the mixed composition, and/or the second composition may be selected from the group consisting of insoluble inorganic metal salts, metal oxides, minerals and insoluble polymer particles. The one or more particulate substances of the first composition, the hair treatment composition, the mixed composition, and/or the second composition may be titanium dioxide.

The one or more particulate substances of the first composition, the hair treatment composition, the mixed composition, and/or the second composition may be present in the first composition, the hair treatment composition, the mixed composition, and/or the second composition in an undissolved, or a stably dispersed form, and, following application to the hair and evaporation of the solvent, can deposit on the hair in a solid form.

The one or more particulate substances of the first composition, the hair treatment composition, the mixed composition, and/or the second composition may be selected from the group consisting of silica (silica gel, silicon dioxide) and metal salts, in particular inorganic metal salts. The particulate substance of the first composition, the hair treatment composition, the mixed composition, and/or the second composition may be silica. The one or more particulate substances of the first composition, the hair treatment composition, the mixed composition, and/or the second composition may be selected from the group consisting of metal salts such as alkali metal or alkaline earth metal halides, e.g. sodium chloride or potassium chloride; alkali metal or alkaline earth metal sulfates, such as sodium sulfate or magnesium sulfate.

Solvent

The first composition, the hair treatment composition, the mixed composition, and/or the second composition may further comprise one or more solvents. The one or more solvents may be selected from water, or a mixture of water and at least one organic solvent to dissolve the compounds that would not typically be sufficiently soluble in water.

Suitable organic solvents for the first composition, the hair treatment composition, the mixed composition, and/or the second composition may include, but are not limited to: from $C_2$ to $C_4$ lower alkanols (such as ethanol, propanol, isopropanol); aromatic alcohols (such as benzyl alcohol and phenoxyethanol); polyols and polyol ethers (such as carbitols, 2-butoxyethanol, propylene glycol, propylene glycol monomethyl ether, diethylene glycol monoethyl ether, monomethyl ether, hexylene glycol, glycerol, ethoxy glycol, butoxydiglycol, ethoxydiglycerol, dipropyleneglocol, polyglycerol); propylene carbonate; and mixtures thereof.

The one or more solvents of the first composition, the hair treatment composition, the mixed composition, and/or the second composition may be selected from the group consisting of water, ethanol, propanol, isopropanol, glycerol, 1,2-propylene glycol, hexylene glycol, ethoxy diglycol, and mixtures thereof.

Typically, the first composition, the hair treatment composition, the mixed composition, and/or the second composition may comprise water as a main ingredient, particularly in a total amount ranging from at least 50%, alternatively from at least 60%, alternatively from at least 70%, by total weight of the respective composition. Typically, when present, the first composition, the hair treatment composition, the mixed composition, and/or the second composition may comprise a total amount of organic solvents ranging from 1% to 30%, by total weight of the respective composition.

Radical Scavenger

The first composition, the hair treatment composition, the mixed composition, and/or the second composition may comprise one or more radical scavengers. The one or more radical scavengers of the first composition, the hair treatment composition, the mixed composition, and/or the second composition may be present in a sufficient amount to reduce damage to the hair during an oxidative bleaching or coloring process.

The one or more radical scavengers may be a species that can react with a radical species, particularly a carbonate radical to convert the radical species by a series of fast reactions to a less reactive species. The one or more radical scavengers may be advantageously selected such that the one or more radical scavengers are different from an alkalising agent and/or is present in an amount sufficient to reduce the damage to the hair during the coloring/bleaching process.

The one or more radical scavengers of the first composition and/or the second composition may be selected from the group consisting of: benzylamine, glutamic acid, imidazole, di-tert-butylhydroxytoluene, hydroquinone, catechol, and mixtures thereof.

Peroxymonocarbonate Ions

The first composition, the hair treatment composition, the mixed composition, and/or the second composition may further comprise a source of carbonate ions, carbamate ions, hydrogen carbonate ions, and mixtures thereof in a sufficient amount to reduce damage to the hair during the coloring process.

The first composition, the hair treatment composition, the mixed composition, and/or the second composition may particularly comprise at least one source of peroxymonocarbonate ions. Peroxymonocarbonate ions may be formed in situ from a source of hydrogen peroxide and a carbonate ion source. The first composition, the hair treatment composition, the mixed composition, and/or the second composition may comprise a source of carbonate ions or carbamate ions or hydrocarbonate ions or any mixtures thereof. The source of peroxymonocarbonate ions may be selected from the group consisting of sodium, potassium, guanidine, arginine, lithium, calcium, magnesium, barium, ammonium salts of carbonate, carbamate and hydrocarbonate ions, and mixtures thereof.

The carbonate ion source for peroxymonocarbonate ions may be selected from the group consisting of sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate, and mixtures thereof. Percarbonate salts may also be utilized to provide both the source of carbonate ions and oxidizing agent. The source of carbonate ions, carbamate and hydrocarbonate ions may be selected from the group consisting of: sodium hydrogen carbonate, potassium hydrogen carbonate, ammonium carbamate, and mixtures thereof.

Surfactant

The first composition, the hair treatment composition, the mixed composition, and/or the second composition may comprise one or more surfactants. A surfactant can help to provide an emulsion. The first composition, the hair treatment composition, the mixed composition, and/or the second composition may be in the form of an emulsion.

The first composition, the hair treatment composition, the mixed composition, and/or the second composition may be in the form of a cream or gel. The first composition, the hair treatment composition, the mixed composition, and/or the second composition may have a lamellar structure and/or may have a gel network. The first composition, the hair treatment composition, the mixed composition, and/or the second composition may comprise micelles comprising a hydrophobic phase (see the description of the hydrophobic phase more below).

The first composition, the hair treatment composition, the mixed composition, and/or the second composition may comprise from 0.001% to 10%, or from 0.1% to 8%, or from 0.5% to 5%, or from 0.4% to 2%, or from 0.8% to 1.5% of the one or more surfactants by total weight of the respective composition.

The first composition, the hair treatment composition, the mixed composition, and/or the second composition may comprise one or more surfactants which are selected from the group consisting of anionic surfactants, non-ionic surfactants, amphoteric surfactants, zwitterionic surfactants, cationic surfactants, and mixtures thereof. The one or more surfactants of the first composition, the hair treatment composition, the mixed composition, and/or the second composition can be useful for stabilizing a hydrophobic phase in the first composition and/or the second composition, e.g. for stabilizing the gel network and/or lamellar structure.

The first composition, the hair treatment composition, the mixed composition, and/or the second composition may comprise an anionic surfactant. The anionic surfactant of the first composition, the hair treatment composition, the mixed composition, and/or the second composition may be sodium lauryl sulfate or sodium laureth sulfate.

The one or more surfactants of the first composition, the hair treatment composition, the mixed composition, and/or the second composition may be a non-ionic surfactant. The non-ionic surfactant may be selected from the group consisting of lanolin alcohol, and polyoxyethylene ethers of fatty alcohols, and mixtures thereof. The non-ionic surfactant may be particularly ceteareth-n, wherein n is from 2 to 100, or from 10 to 30. When the one or more surfactants of the first composition and/or the second composition are non-ionic, precipitation of others ingredients of the first composition, the hair treatment composition, the mixed composition, and/or the second composition can be prevented.

The first composition, the hair treatment composition, the mixed composition, and/or the second composition may comprise from 0.001% to 5%, or from 0.01% to 3%, or from 0.01% to 1%, or from 0.05% to 1%, or from 0.1% to 0.5%, or from 0.1% to 0.3% of a non-ionic surfactant by total weight of the respective composition. The non-ionic surfactant of the first composition, the hair treatment composition, the mixed composition, and/or the second composition may be selected from the group consisting of lanolin alcohol, and polyoxyethylene ethers of fatty alcohols, and mixtures thereof.

The non-ionic surfactant of the first composition, the hair treatment composition, the mixed composition, and/or the second composition may be a castor oil having polyethylene glycol ether groups or polypropylene glycol ether groups. The polyethylene glycol ether groups of the non-ionic surfactant may be ethers of PEG-n groups, wherein n is an integer of from 2 to 12, or from 2 to 10, or from 3 to 8. When the total M.Wt. of polyethylene glycol ether groups is below 400 Da, the mixing of the first composition, the hair treatment composition, the mixed composition, and/or the second composition can be eased.

The polypropylene glycol ether groups may be ethers of PPG-n groups, wherein n is an integer of from 2 to 60, or from 10 to 50, or from 20 to 40. The polyethylene glycol ether groups or polypropylene glycol ether groups may be selected from the group consisting of: PPG-4, PPG-6, PEG-5, PEG-6, PEG-8, and mixtures thereof. The first composition, the hair treatment composition, the mixed composition, and/or the second composition may comprise PEG-40 Hydrogenated Castor Oil and/or PEG-60 Castor Oil and/or PEG-35 Castor Oil as non-ionic surfactant.

Thickening Agent

The first composition, the hair treatment composition, the mixed composition, and/or the second composition may comprise one or more thickening agents. Thickening agents can help to provide the desired rheology for the first composition, the hair treatment composition, the mixed composition, and/or the second composition, which is useful in terms of mixing and anti-drip. The first composition, the hair treatment composition, the mixed composition, and/or the second composition may comprise from 0.01% to 5% of the one or more thickening agents by total weight of the respective composition. The one or more thickening agents of the first composition, the hair treatment composition, the mixed composition, and/or the second composition may be a thickening polymer.

The first composition, the hair treatment composition, the mixed composition, and/or the second composition may comprise from 0.1% to 2% of a thickening polymer by total weight of the respective composition. The thickening polymer of the first composition, the hair treatment composition, the mixed composition, and/or the second composition may be an associative polymer. The thickening polymer of the first composition, the hair treatment composition, the mixed composition, and/or the second composition may also serve as conditioning agents, as described below.

According to an embodiment, the concentration of the thickening agent is higher in the second composition relative to the first composition. The first composition is typically mixed with the hair treatment composition so that the rheology of the resulting mixed composition is mainly determined by the mixture of the first composition and the hair treatment compositions. The second composition is typically applied as such without mixing with a hair treatment composition. To improve handling of the second composition and to avoid dripping-off of the second composition when applied to the hair, the second composition may be made more viscous than the first composition.

Conditioning Agent

The first composition, the hair treatment composition, the mixed composition, and/or the second composition may comprise one or more conditioning agents. The one or more conditioning agents of the first composition, the hair treatment composition, the mixed composition, and/or the second composition may be selected from the group consisting of silicone materials, amino silicones, fatty alcohols, polymeric resins, polyol carboxylic acid esters, cationic polymers, cationic surfactants, insoluble oils and oil derived materials and mixtures thereof. The one or more conditioning agents of the first composition, the hair treatment composition, the mixed composition, and/or the second composition may be selected from the group consisting of mineral oils, glycerine, sorbitol and mixtures thereof.

The first composition, the hair treatment composition, the mixed composition, and/or the second composition may comprise from 0.05% to 20%, or from 0.1% to 15%, or from 0.2% to 10%, or from 0.2% to 2%, or from 0.5% to 2% of the one or more conditioning agents by total weight of the respective composition. The one or more conditioning agents may be included in a separate pre- and/or post-treatment composition.

Suitable conditioning agents may include, but are not limited to: silicones, aminosilicones, fatty alcohols, polymeric resins, polyol carboxylic acid esters, cationic polymers, cationic surfactants, insoluble oils and oil derived materials and mixtures thereof. Additional conditioning agents may include mineral oils and other oils such as glycerin and sorbitol.

Particularly useful conditioning agents for the first composition, the hair treatment composition, the mixed composition, and/or the second composition may be cationic polymers and/or silicones. Cationic polymers may be chosen from those comprising units of at least one amine group chosen from primary, secondary, and tertiary amine groups and quaternary ammonium groups that may either form part of the main polymer chain, or be borne by a side substituent that is directly attached to the main polymer chain.

The one or more conditioning agents of the first composition, the hair treatment composition, the mixed composition, and/or the second composition may be a silicone. The silicone of the first composition, the hair treatment composition, the mixed composition, and/or the second composition may be selected from the group consisting of polyalkylsilioxane oils, linear polydiemthylsiloxane oils containing trimethylsilyl or hydroxydimethylsiloxane end-groups, polymethylphenylsiloxane polydimethylphenylsiloxane, polydimethyldiphenylsiloxane oils, silicone resins, organofunctional siloxanes having in their general structure one or a number of organofunctional group(s), the same or different, attached directly to the siloxane chain, and mixtures thereof. Said organofunctional group(s) may be selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric, betain groups and mixtures thereof. The silicone of the first composition, the hair treatment composition, the mixed composition, and/or the second composition may be either used as a neat fluid or in the form of an pre-formed emulsion.

According to an embodiment, the first composition is substantially free of, or is free of, fatty acids and/or silicones.

Cosmetically Acceptable Carrier

The first composition, the hair treatment composition, the mixed composition, and/or the second composition comprises a cosmetically acceptable carrier. The cosmetically acceptable carrier of the first composition, the hair treatment composition, the mixed composition, and/or the second composition may be an aqueous carrier. The first composition, the hair treatment composition, the mixed composition, and/or the second composition may comprise water. Water can provide a hydrophilic phase, which the hydrophilic portions of any other ingredients comprised in the first composition, the hair treatment composition, the mixed composition, and/or the second composition can interact with water. Water can also provide a fluid phase meaning that the first composition, the hair treatment composition, the mixed composition, and/or the second composition can be in liquid form and therefore easily mixed with other fluid compositions such as an oxidizing composition. The first composition, the hair treatment composition, the mixed composition, and/or the second composition may comprise from 50% to 85% water, or from 65% to 75% of water by total weight of the respective composition.

The cosmetically acceptable carrier may be any carrier suitable for formulating the first composition, the hair treatment composition, the mixed composition, and/or the second composition being suitable for application onto hair. The cosmetically acceptable carrier may be selected from either an aqueous medium or an aqueous-alcoholic medium. When the cosmetically acceptable carrier is an aqueous-alcoholic carrier, the cosmetically acceptable carrier may comprise water and an alcohol. An alcohol can advantageously influence the viscosity of a relatively wide spectrum of ingredients of the first composition, the hair treatment composition, the mixed composition, and/or the second composition. The alcohol of the first composition, the hair treatment composition, the mixed composition, and/or the second composition may be selected from the group consisting of: ethanol, isopropanol, propanol, and mixtures thereof.

When the cosmetically acceptable carrier is an aqueous carrier, the aqueous carrier may consist essentially of water and may be substantially free of alcohol. The first composition, the hair treatment composition, the mixed composition, and/or the second composition may comprise a safe and effective amount of cosmetically acceptable carrier which is water. The first composition, the hair treatment composition, the mixed composition, and/or the second composition may comprise from 0.1% to 99%, or from 1% to 98%, or from 10% to 97%, or from 30% to 95% of water by total weight of the respective composition.

The first composition, the hair treatment composition, the mixed composition, and/or the second composition may be substantially free of alcohol, such as volatile alcohols (e.g. ethanol, isopropanol, propanol). When the first composition, the hair treatment composition, the mixed composition, and/or the second composition is substantially free of alcohol, the first composition, the hair treatment composition, the mixed composition, and/or the second composition can have advantageously a reduced odour. Flammability issues can also be prevented.

The cosmetically acceptable carrier of the first composition, the hair treatment composition, the mixed composition, and/or the second composition may be an oily compound. The oily compound may be selected from the group consisting of cyclic silicones and volatile hydrocarbons. Cyclic silicones can be available from Dow Corning. The cyclic silicone may have from at least 3 silicone atoms or from at least 5 silicone atoms but no more than 7 silicone atoms or no more than 6 silicone atoms. The cyclic silicone may conform to the formula:

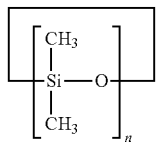

wherein n is from 3 or from 5 but no more than 7 or no more than 6. The cyclic silicone may have a kinematic viscosity of less than 10 cSt at 23° C. A Suitable cyclic silicone for use herein may include Cyclomethicone D5 (commercially available from G.E. Silicones). Alternatively, the first composition, the hair treatment composition, the mixed composition, and/or the second composition may be silicone-free.

Volatile hydrocarbons e.g. Isopar can be obtained from ExxonMobil Petroleum and Chemical. The oily compound may be a mineral oil. Trade names for suitable mineral oils include Benol, Blandol, Hydrobrite, Kaydol (Sonneborn LLC Refined Products), Chevron Superla White Oil (Chevron Products Company), Drakeol, Parol (Calumet Penreco LLC), Peneteck (Calumet Penreco LLC), Marcol, and Primol 352 (ExxonMobil Petroleum and Chemical).

Hydrophobic Phase

The first composition, the hair treatment composition, the mixed composition, and/or the second composition may comprise a hydrophobic phase. The hydrophobic phase of the first composition, the hair treatment composition, the mixed composition, and/or the second composition may be selected from the group consisting of fatty alcohols, fatty acids, and mixtures thereof. The fatty alcohols and/or fatty acids may comprise from 10 to 30, or from 12 to 20, or from 16 to 18 carbon atoms. The hydrophobic phase of the first composition, the hair treatment composition, the mixed composition, and/or the second composition may comprise two different fatty alcohols. The hydrophobic phase of the first composition, the hair treatment composition, the mixed composition, and/or the second composition may comprise two different fatty alcohols, both comprising from 10 to 14 carbons.

According to an embodiment, the first composition is substantially free of, or is free of, fatty acids.

Preservative

The first composition, the hair treatment composition, the mixed composition, and/or the second composition may comprise at least one preservative and/or a mixture of preservatives. The first composition, the hair treatment composition, the mixed composition, and/or the second composition may comprise from 0.01% to 1% preservative, or from 0.1% to 0.5% preservative by total weight of the respective second composition. The preservative of the first composition, the hair treatment composition, the mixed composition, and/or the second composition may be selected from the group consisting of benzyl alcohol, phenoxyethanol, 1,3-bis(hydroxymethyl)-5,5-dimethylimidazolidine-2,4-dione, and mixtures thereof. The first composition, the hair treatment composition, the mixed composition, and/or the second composition may comprise at least one preservative; and wherein the preservative may be selected from the group consisting of benzyl alcohol, phenoxyethanol, and mixtures thereof; or wherein the preservative may be a mixture of benzyl alcohol and phenoxyethanol. The first composition, the hair treatment composition, the mixed composition, and/or the second composition may be substantially free of benzoate compounds. Indeed, having benzoate compounds can help to prevent instability and/or precipitation of the first composition, the hair treatment composition, the mixed composition, and/or the second composition. The first composition, the hair treatment composition, the mixed composition, and/or the second composition may be substantially free of parabens.

Perfume

The first composition, the hair treatment composition, the mixed composition, and/or the second composition may comprise a perfume. The first composition, the hair treatment composition, the mixed composition, and/or the second composition may comprise from 0.001% to 2% of a perfume by total weight of the respective first composition, the hair treatment composition, the mixed composition, and/or the second composition. Perfume can provide an enhanced user experience by making the composition smell pleasant and/or invoke emotions tailored to the visual effects on the fibers, such as relaxing or exciting smells.

Alternatively, the first composition, the hair treatment composition, the mixed composition, and/or the second composition may be substantially free of perfume and/or fragrance. Some consumers prefer perfume-free compositions.

The perfume of the first composition, the hair treatment composition, the mixed composition, and/or the second composition may be an animal fragrance or a plant fragrance. The animal fragrance may be selected from the group consisting of musk oil, civet, castoreum, ambergris, and mixtures thereof.

The plant fragrance may be selected from the group consisting of nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract, and mixtures thereof.

The perfume of the first composition, the hair treatment composition, the mixed composition, and/or the second composition may be selected from the group consisting of acetophenone, adoxal, aldehyde C-12, aldehyde C-14, aldehyde C-18, allyl caprylate, ambroxan, amyl acetate, dimethylindane derivatives, a-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronnellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral, majantol, mayol, melonal, menthol, p-methylacetophenone, methyl anthranilate, methyl cedrylone, methyl dihydrojasmonate, methyl eugenol, methyl ionone, methyl-α-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, γ-undecalactone, undecenal, vanillin, veloutone, verdox, and mixtures thereof.

Viscosity

The first composition, the hair treatment composition, the mixed composition, and/or the second composition may have a kinematic viscosity of from 0.5 cSt to 1500 cSt, measured at 23° C. according to the following method. "Viscosity" can mean dynamic viscosity (measured in mPa·s) or kinematic viscosity (measured in centistokes, cSt) of a liquid at 23° C. and ambient conditions. Dynamic viscosity may be measured using a rotational viscometer, such as a Brookfield Dial Reading Viscometer Model 1-2 RVT available from Brookfield Engineering Laboratories (USA) or other substitutable model as known in the art. Typical Brookfield spindles which may be used include, without limitation, RV-7 at a spindle speed of 20 rpm, recognizing that the exact spindle may be selected as needed by one skilled in the art. Kinematic viscosity may be determined by dividing dynamic viscosity by the density of the liquid (at 23° C. and ambient conditions), as known in the art.

The viscosity of the first composition, the hair treatment composition, the mixed composition, and/or the second composition may be useful in view of enabling the first composition, the hair treatment composition, the mixed composition, and/or the second composition to be readily applied to the hair fibers—e.g. spread evenly onto the hair. Viscosity can be influenced by the level of cosmetically acceptable carrier in the first composition, the hair treatment composition, the mixed composition, and/or the second composition and the level of the thickening agent.

The first composition, the hair treatment composition, the mixed composition, and/or the second composition may have a kinematic viscosity of from 1 cSt to 1000 cSt. The first composition, the hair treatment composition, the mixed composition, and/or the second composition may have a kinematic viscosity of from 1.5 cSt to 500 cSt, or from 2 cSt to 350 cSt, or from 2.5 cSt to 200 cSt, or from 3 cSt to 150 cSt, measured at 23° C. 1 centistoke (cSt) is equal to $1 \times 10^6$ m$^2$/s).

The first composition, the hair treatment composition, the mixed composition, and/or the second composition may have a dynamic viscosity of from 1 mPa·s to 5000 mPa·s. The first composition, the hair treatment composition, the mixed composition, and/or the second composition may have a viscosity of from 2 mPa·s to 400 mPa·s, or from 3 mPa·s to 100 mPa·s. Alternatively, the first composition, the hair treatment composition, the mixed composition, and/or the second composition may have a dynamic viscosity of from 30 mPa·s to 250 mPa·s, or from 100 mPa·s to 200 mPa·s.

This viscosity range of the first composition, the hair treatment composition, the mixed composition, and/or the second composition may be useful in view of helping to prevent the first composition, the hair treatment composition, the mixed composition, and/or the second composition from dripping. When the viscosity is too high, the first composition and/or the second composition may not be readily mixed, e.g. with the cosmetically acceptable carrier, where present.

According to an embodiment, the second composition has a higher viscosity than the first composition.

Volatility

The first composition, the hair treatment composition, the mixed composition, and/or the second composition may be substantially free of compounds having a vapor pressure below 0.01 mmHg, or below 0.001 mm Hg, measured at 23° C. and 1 atm. Having the first composition, the hair treatment composition, the mixed composition, and/or the second composition having a relatively low volatility can help to reduce the odour of the first composition, the hair treatment composition, the mixed composition, and/or the second composition and also can help to provide a relatively safer safety profile.

Rheology

The first composition, the hair treatment composition, the mixed composition, and/or the second composition may further comprise a hydrophobic phase, a hydrophilic phase, one or more surfactants, and one or more thickening polymers capable of interacting with the hydrophobic phase and the hydrophilic phase, wherein the composition has a storage modulus of at least 3000 Pa, or at least 3300 Pa, or at least 3500 Pa, or at least 4000 Pa, or at least 4500 Pa, or at least 5000 Pa, measured by frequency sweep at an angular frequency of 0.6 rad/s at 23° C., and wherein the one or more thickening polymers are an associative thickening polymer and comprise hydrophobic moieties and hydrophilic moieties. The storage modulus may be not more than 10 kPa, or 9 kPa, or 8 kPa, or 7 kPa, or 6 kPa, measured by frequency sweep at an angular frequency of 0.6 rad/s at 23° C. The hydrophilic moieties of the associative thickening polymer may comprise urethane units.

First and Second Composition

According to an embodiment, the first composition is substantially free of, or is free of, a further component different to the at least be-functional carboxylic acid, or the cosmetically acceptable salts thereof. The further component optionally not contained in first composition is selected from the group of diamines, polyamines, primary amines, fatty acids, silicones, oxidative dye precursors, direct dyes, reducing agents, unsaturated compounds having one or more carboxylic acid groups, and mixtures thereof. The further component optionally not contained in first composition may be selected from primary amines, secondary amines, and tertiary amines. According to an embodiment, the first composition may comprise quaternary "ammonium" compounds.

The first composition is mixed with the hair treatment composition, which can be a commercially available hair treatment composition for coloring, bleaching or permanent waving the hair. To avoid unwanted reactions with components of the hair treatment composition, the composition of the first composition can be limited to components that do not significantly interfere, or react, with certain components of the hair treatment composition.

For example, avoiding diamines, polyamines, primary amines in the first compositions as further components reduces possible unwanted reactions with dye precursors or coloring agents of the hair treatment composition as the amount of reactive amines is reduced. According to an embodiment, the first composition is therefore substantially free of, or is free of, diamines, polyamines, primary amines, secondary amines, and/or tertiary amines.

Furthermore, unsaturated compounds having one or more carboxylic acid groups may not be sufficiently stable in the first composition and may react with other components of the first composition or the hair treatment composition. According to an embodiment, the first composition is therefore substantially free of, or is free of, unsaturated compounds having one or more carboxylic acid groups such as unsaturated carboxylic acids.

Moreover, fatty acids and/or silicones may also influence the hair treatment composition. According to an embodiment, the first composition is therefore substantially free of, or is free of, fatty acids and/or silicones.

According to an embodiment, the second composition may also be substantially free of, or be free of, a further component selected from diamines, polyamines, primary amines, secondary amines, and/or tertiary amines. According to an embodiment, both the first composition and the second composition may be substantially free of, or be free of, a further component selected from diamines, polyamines, primary amines, secondary amines, and/or tertiary amines. According to an embodiment, the first and/or second composition may comprise quaternary "ammonium" compounds.

Kit

According to an embodiment, a kit for treating hair comprises:
(1) a first composition as defined hereinbefore;
(2) a second composition as defined hereinbefore.

The first composition and the second composition are separately packaged.

The kit may further comprise (3) a conditioning composition comprising one or more conditioning agents. Conditioning agents have already been described above.

The kit may further comprise (4) a thickening composition. Such thickening compositions are currently on the market as under the brand "Color.id" from Wella Professionals. The thickening composition of the kit may comprise one or more thickening polymers capable of interacting with the hydrophobic phase and the hydrophilic phase.

The kit may further comprise a mixing receptacle and/or a mixing means. The mixing receptacle of the kit may be a bowl. The mixing means of the kit may be a spatula.

The first composition (1) and the second composition (2) may be packaged in separate sealed containers. The first composition (1) may be packaged in a flexible tube packaging composed of metal, plastics or a combination thereof. The second composition (2) may be packaged in a squeezable container. The squeezable container may have at least 50% headspace. The squeezable container may have a headspace being at least the volume of the first composition (1). The first composition may be packaged in a plastic container according to claim 1 of European Patent Application EP 2 801 281 A1, wherein the plastic container has two symmetrical collapsible side panels and a non-collapsible squeezable back panel; wherein the ratio of the average thicknesses between front and/or back panels and the side panels is at least 2:1 (EP 2 801 281 A1 paragraphs [0025] to [0044] as well as the Figures are incorporated herein by reference). The plastic container has the advantage that it is resistant to random, uncontrolled deformation under a substantial pressure differential between the environment and inside the container, yet having an affordable cost of manufacture and/or being appealing to the consumer.

The method may be carried out from sequentially applied to the hair, the first composition as stated hereinbefore and the second composition as stated hereinbefore.

In the kit, the one or more at least bi-functional carboxylic acid may be selected from the group consisting of Oxalic Acid, Malonic Acid, Succinic Acid, Glutaric Acid, Adipic Acid, Pimelic Acids, Suberic Acid, Azelaic Acid, Sebacic Acid, Maleic Acid, Fumaric Acid, Glutaconic Acid, Traumatic Acid, Muconic Acid, Glutinic Acid, Citracronic Acid, Mesaconic Acid, Malic Acid, Aspartic Acid, Glutamic Acid, Tartronic Acid, Tartaric Acid, Diaminopimelic Acid, Saccharic Acid, Mesoxalic Acid, Oxaloacetic Acid, Acetonedicarboxylic Acid, Arabinaric Acid, Phthalic Acid, Isophthalic Acid, Terephthalic Acid, Diphenic Acid, 2,6-Naphthalenedicarboxylic Acid, Citric Acid, Isocitric Acid, Aconitic Acid, Propane-1,2,3-tricarboxylic Acid, Trimesic Acid, Methanetetracarboxylic Acid, 1,2,3,4-Benzenetetracarboxylic Acid, 2,2'-(ethane-1,2-diylbis(azanediyl))disuccinic Acid, Aspergillomarasine Acid, Ethylenetetracarboxylic Acid, or derivatives thereof, or cosmetically acceptable salts thereof.

Experimental

Hair Strands

Ponytail Hair strands having a width of 5 cm and a length of 10 cm, available from *International Hair Importers &*

*Products*, Glendale, N.Y., mass: 1.8 g±0.05 g, characteristics: cysteic acid: 17.4-18.1 µmol/g hair; medullated hair, ϕ: 60-80 µm, were used.

Pre-Treatment (Bleaching Process)

The hair strands were weighed and then soaked in a mixture of 2.5 g bleaching powder and 7.5 ml Wella Welloxyd™ per 1 g of hair (in a lab basin). It has to be carried out in an extractor hood. The concentration of hydrogen peroxide in Wella Welloxyd™ was 9%. The residence time during the bleaching step was 30 min. The hair strands were turned upside down after each 7.5 min. After bleaching the hair strands were rinsed under tap water (6 L/min, 35° C.) for 2 min. The bleaching process was carried out three times in which the second bleaching step followed immediately after the first bleaching step and the third bleaching step followed immediately after the second bleaching step. Before the $2^{nd}$ and the $3^{rd}$ bleaching step was started, the hair was dabbed with a napkin. Subsequently the hair strands were washed twice with 0.25 ml standard-shampoo (10% Na-laurylether-sulfate, 4% NaCl) per 1 g hair for 1 minute, rinsed for 1 minute. Then the hair strands were stored in distilled water for 24 h. After that the hair strands were rinsed for 2 min under tap water (6 L/min, 35° C.). Finally the hair strands were dried at 20° C. and 65% relative humidity at least overnight.

Hair Softness Test

The efficacy of the new method for treating hair was tested using the Hair Softness Tester as described in EP 2990796 A1. For each experiment sample, 4 hair tresses are used.

Four experiment samples are carried out comparing the effectiveness of the first composition and the second composition according to embodiments. The first composition comprises Malic Acid as an at least bi-functional carboxylic acid in a concentration of 9% by weight. The pH of the first composition is adjusted to pH 9 using an effective amount of sodium hydroxide. For the purpose of the test, such first composition is referred to as STEP (a). As a reference for STEP (a), a STEP (a') formulation was created that contains only an effective amount of sodium hydroxide to adjust the pH of such "placebo first composition" to pH 9. The second composition comprises Malic Acid as an at least bi-functional carboxylic acid in a concentration of 3% by weight. The pH of the second composition is adjusted to pH 4 using an effective amount of sodium hydroxide. For the purpose of the test, such second composition is referred to as STEP (b). As a reference for STEP (b), a STEP (b') formulation was created that contains only an effective amount of sodium hydroxide to adjust the pH of such "placebo second composition" to pH 4. As a reference for all experiments "untreated" hair samples were used which were only treated according to the pre-treating method described. When Step (a), Step (a'), Step (b), or Step (b') were carried out, the hair samples were first immersed in either the first composition or the placebo first composition for 5 minutes, then taken out and dabbed with a napkin, then placed into either the second composition or the placebo second composition. After that the hair strands were rinsed for 2 min under tap water (6 L/min, 35° C.). Finally the hair strands were dried at 20° C. and 65% relative humidity at least overnight.

Each hair tress is passed in an S-shape between the rods of the device according to EP 2990796 A1 at an extension of 400 mm/min. The measurement is executed 5 times in stationary mode and 5 times in rotational mode. The forces exerted are calculated as total work (energy). The work in the rotational mode relates to the hair stiffness. The lower the stiffness of the hair tresses, the higher its elasticity is.

Without wishing to be bound by theory it is believed that the at least bi-functional carboxylic acid, or cosmetically acceptable salt thereof, can initially cross-link the amino- and ammonium-groups of the hair proteins, thus improving its mechanical properties expressed as reduced stiffness. A significance tests using a standard T-Test protocol is carried out to assess differences. Statistical significance tested to 95% confidence interval.

| Average [mJ] | Standard Deviation [mJ] | N | Samples | Sample 1 | Sample 2 | Sample 3 |
|---|---|---|---|---|---|---|
| 17.66 | 0.191 | 4 | Sample 1 | | | |
| 14.68 | 0.195 | 4 | Sample 2 | 100.0% | | |
| 15.08 | 0.150 | 4 | Sample 3 | 100.0% | 98.3% | |
| 12.98 | 0.389 | 4 | Sample 4 | 100.0% | 100.0% | 100.0% |

Sample 1: Untreated
Sample 2: Step (a') followed by Step (b)
Sample 3: Step (a) followed by Step (b')
Sample 4: Step (a) followed by Step (b)

Conclusions: the presence of an at least bi-functional carboxylic acid, or cosmetically acceptable salt thereof, significantly reduces the stiffness of hair, thus improves it elasticity. The effect can be realized via the application of the at least bi-functional carboxylic acid either at basic or acid pH.

The same 4 samples were tested for hair softness and hair. 4 replicates each were used. The assessment was performed by 5 trained individuals using a 5-point score, where "5" denotes best hair softness or best hair shine.

| Sample | Hair Softness [score] | Hair Shine [score] |
|---|---|---|
| Sample 1 | 2.2 | 3.0 |
| Sample 2 | 2.6 | 2.8 |
| Sample 3 | 2.6 | 2.8 |
| Sample 4 | 3.2 | 4.0 |

Conclusions: the presence of an at least bi-functional carboxylic acid, or cosmetically acceptable salt thereof, improves hair softness and hair shine. The effect can be realized via the application of the at least bi-functional carboxylic acid either at basic or acid pH.

A test of the benefits of a high pH first composition for improved hair bleaching, when mixed with commercially available hair bleach, was carried out. The respective first composition is mixed with commercially available hair bleach and the result is assessed by 10 trained professional stylists for bleach effectiveness. The following 6 different first compositions were used:
1. First Composition FC1: Reference, Water only, pH 7
2. FC2: "BondPro+" Protection Serum, commercially available from Goldwell, Germany, pH 3.7
3. FC3: "Fiberplex" Bond Booster, commercially available from Schwarzkopf, Germany, pH 3.8
4. FC4: "Olaplex" Bond Multiplier, commercially available from Olaplex, USA, pH 3.9
5. FC5: "Smartbond" Bond Strengthening System, Step 1, commercially available from L'Oreal, France, pH 3.0
6. FC6: A water based 9% solution of Malic Acid, adjusted to pH 9 with sodium hydroxide 6 different mixed compositions are prepared. For this, 30 g of commercially available Wella Blondor Multi Blond Powder is mixed with 45 g of Wella Welloxon Oxidation Crème 6% and 6 g of the respective first composition. The pH of the resulting mixed composition is measured.

1. Mixed Composition MC1: 30 g of commercially available Wella Blondor Multi Blond Powder+45 g Wella Welloxon Oxidation Crème 6%+6 g of FC1;
2. MC2: 30 g of commercially available Wella Blondor Multi Blond Powder+45 g Wella Welloxon Oxidation Crème 6%+6 g of FC2;
3. MC3: 30 g of commercially available Wella Blondor Multi Blond Powder+45 g Wella Welloxon Oxidation Crème 6%+6 g of FC3;
4. MC4: 30 g of commercially available Wella Blondor Multi Blond Powder+45 g Wella Welloxon Oxidation Crème 6%+6 g of FC4;
5. MC5: 30 g of commercially available Wella Blondor Multi Blond Powder+45 g Wella Welloxon Oxidation Crème 6%+6 g of FC5;
6. MC6: 30 g of commercially available Wella Blondor Multi Blond Powder+45 g Wella Welloxon Oxidation Crème 6%+6 g of FC6;

|     | Number | Mean  | Std Dev  | Std Err Mean | Lower 95% | Upper 95% |
| --- | ------ | ----- | -------- | ------------ | --------- | --------- |
| MC1 | 10     | 10.35 | 0.265976 | 0.08411      | 10.16     | 10.54     |
| MC2 | 11     | 9.98  | 0.178157 | 0.05372      | 9.86      | 10.10     |
| MC3 | 10     | 9.99  | 0.175043 | 0.05535      | 9.87      | 10.12     |
| MC4 | 12     | 10.05 | 0.204560 | 0.05905      | 9.92      | 10.18     |
| MC5 | 10     | 9.90  | 0.410360 | 0.12977      | 9.61      | 10.20     |
| MC6 | 12     | 10.32 | 0.224424 | 0.06479      | 10.18     | 10.47     |

Conclusion: When the first composition has a pH of 3 to 4, the ph of the mixed composition is reduced by >0.3 pH units. The differences are statistically significant at 95% confidence interval.

| Connecting Letters Report | | |
| --- | --- | --- |
| | | Mean |
| MC1 | A | 10.349000 |
| MC6 | A | 10.322500 |
| MC4 | B | 10.049167 |
| MC3 | B | 9.992000 |
| MC2 | B | 9.980000 |
| MC5 | B | 9.902000 |

Levels not connected by same letter are significantly different.

Mixed compositions MC2, MC3, MC4, MC5, MC6 were applied in a half-head comparison test to the left side of female clients and compared to mixed composition MC1 applied to the right side of the same clients' heads. Mixed compositions were left on head for 30 minutes, followed by 2 minutes rinsing with regular tab water, followed by application of the commercially available second composition of the respective manufactures product system on the left and on the right side of the respective client. After a dwell-time of 10 minutes the hair was rinsed with regular tab water for 2 minutes again, and the hair shampooed with Wella Color Brilliance shampoo. After shampooing, the hair is dried and styled as normal and the Bleach result assessed by 10 trained professional stylists for its respective bleach performance. A preference rating was given.

| Left | Right | Preference |
| --- | --- | --- |
| MC2 | MC1 | Right (MC1) |
| MC3 | MC1 | Right (MC1) |
| MC4 | MC1 | Right (MC1) |
| MC5 | MC1 | Right (MC1) |
| MC6 | MC1 | No preference |

Conclusion: When the first composition has a pH of 3 to 4, the pH of the mixed composition is reduced by >0.3 pH units and the hair bleach performance is reduced.

A test of the benefits of a high pH first composition for improved hair coloring, when mixed with commercially available oxidative hair color, was carried out. The respective first composition is mixed with commercially available oxidative hair color and the result is assessed by 10 trained professional stylists for color brilliance. The same first compositions FC1, FC2, FC3, FC3, FC4, FC5, FC6 are used.

6 different mixed compositions are prepared. For this, 30 g of commercially available Wella Koleston Perfect Deep Brown 7/7 is mixed with 30 g of Wella Welloxon Oxidation Crème 6% and 6 g of the respective first composition.

7. Mixed Composition MC7: 30 g of commercially available Wella Koleston Perfect Deep Brown 7/7+30 g Wella Welloxon 6% Oxidation Crème+6 g of FC1;
8. MC8: 30 g of commercially available Wella Koleston Perfect Deep Brown 7/7+30 g Wella Welloxon 6% Oxidation Crème+6 g of FC2;
9. MC9: 30 g of commercially available Wella Koleston Perfect Deep Brown 7/7+30 g Wella Welloxon 6% Oxidation Crème+6 g of FC3;
10. MC10: 30 g of commercially available Wella Koleston Perfect Deep Brown 7/7+30 g Wella Welloxon 6% Oxidation Crème+6 g of FC4;
11. MC11: 30 g of commercially available Wella Koleston Perfect Deep Brown 7/7+30 g Wella Welloxon 6% Oxidation Crème+6 g of FC5;
12. MC12: 30 g of commercially available Wella Koleston Perfect Deep Brown 7/7+30 g Wella Welloxon 6% Oxidation Crème+6 g of FC6;

Mixed compositions MC8, MC9, MC10, MC11, MC12 were applied in a half-head comparison test to the left side of female clients and compared to mixed composition MC7 applied to the right side of the same clients' heads. Mixed compositions were left on head for 30 minutes, followed by 2 minutes rinsing with regular tab water, followed by application of the commercially available second composition of the respective manufactures product system on the left and on the right side of the respective client. After a dwell-time of 10 minutes the hair was rinsed with regular tab water for 2 minutes again, and the hair shampooed with Wella Color Brilliance shampoo. After shampooing, the hair is dried and styled as normal and the hair color result assessed by 10 trained professional stylists for its respective color brilliance and uniformity. A preference rating was given.

| Left | Right | Preference |
| --- | --- | --- |
| MC8 | MC7 | Right (MC7) |
| MC9 | MC7 | Right (MC7) |
| MC10 | MC7 | Right (MC7) |
| MC11 | MC7 | Right (MC7) |
| MC12 | MC7 | No preference |

Conclusion: When the first composition has a pH of 3 to 4 and is mixed with commercially available oxidative hair color, the resulting hair color brilliance and uniformity is reduced.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

The inventor has surprisingly found that when applying sequentially a first composition comprising one or more at least bi-functional carboxylic acids, or cosmetically acceptable salts thereof, wherein the first composition has a pH from 7 to 13, or applying to the hair a second composition comprising in a cosmetically acceptable carrier one or more at least bi-functional carboxylic acids, or cosmetically acceptable salts thereof, wherein the second composition has a pH value of 3 to 7, the stiffness of the hair can be significantly reduced and hair softness and hair shine improved. More surprisingly, the hair stiffness can be even more reduced and hair softness and hair shine even more improved, when the one or more at least bi-functional carboxylic acid, or cosmetically acceptable salt thereof, wherein the first composition has a pH from 7 to 13, and the second composition comprising in a cosmetically acceptable carrier one or more at least bi-functional carboxylic acids, or cosmetically acceptable salts thereof, wherein the second composition has a pH value of 3 to 7, are applied sequentially to hair.

Embodiments

In the following, further aspects, embodiments and features of the invention are described:

Embodiment 1. A method for treating hair comprising the steps of:
(a) mixing a first composition having a pH from 7 to 13 with a hair treatment composition to form a mixed composition, the hair treatment composition comprising one of a bleaching agent, a coloring agent, and a permanent hair waving agent,
(b1) applying to the hair the mixed composition having a pH from 7 to 13, and
(c) applying to the hair a second composition having a pH from 3 to 7,
wherein each of the first and the second composition comprises in a cosmetically acceptable carrier, one or more at least bi-functional carboxylic acids of Formula 1, or cosmetically acceptable salts thereof, or mixtures thereof,
wherein Formula 1 is HOOC—Ra-(O—Rb)n-COOH, wherein Ra is selected from the group consisting of C1-C10 alkylene, C1-C10 cycloalkylene, C1-C10 alkenylene, and C6-C12 (alkyl)arylene, Rb is C2-C4 alkylene, n is an integer from 0 to 4, wherein Ra and/or each Rb optionally are substituted with one or more substituents selected from —COOH, —OH, —NH2, —SH, and =O, and wherein the total number of carbon atoms in Ra plus Rb is 12 or less.

Embodiment 2. The method according to embodiment 1, wherein the difference between the pH of the first composition and the pH of the hair treatment composition is 1.5 or less, particularly 1.2 or less, such as 1.0 or less.

Embodiment 3. The method according to embodiment 1 or 2, wherein the difference between the pH of the hair treatment composition and the pH of the mixed composition is 0.3 or less, particularly 0.2 or less, such as 0.15 or less.

Embodiment 4. The method according to embodiment 1 or 2, wherein the hair treatment composition comprises one or more oxidizing agents.

Embodiment 5. The method according to any of the preceding embodiments, wherein the hair treatment composition comprises oxidative dye precursors including one or more couplers and one or more primary intermediates.

Embodiment 6. The method according to any of the preceding embodiments, wherein the hair treatment composition comprises one or more reducing agents.

Embodiment 7. A method for treating hair comprising the steps of:
(b2) applying to the hair a first composition having a pH from 7 to 13,
(c) applying to the hair a second composition having a pH from 3 to 7,
wherein each of the first and the second composition comprises in a cosmetically acceptable carrier, one or more at least bi-functional carboxylic acids of Formula 1, or cosmetically acceptable salts thereof, or mixtures thereof,
wherein Formula 1 is HOOC—Ra—(O—Rb)n-COOH, wherein Ra is selected from the group consisting of C1-C10 alkylene, C1-C10 cycloalkylene, C1-C10 alkenylene, and C6-C12 (alkyl)arylene, Rb is C2-C4 alkylene, n is an integer from 0 to 4, wherein Ra and/or each Rb optionally are substituted with one or more substituents selected from —COOH, —OH, —NH2, —SH, and =O, and wherein the total number of carbon atoms in Ra plus Rb is 12 or less.

Embodiment 8. The method according to any of the preceding embodiments, wherein the one or more at least bi-functional carboxylic acids, or cosmetically acceptable salts thereof, of the first formulation and of the second formulation are identical.

Embodiment 9. The method according to any of the preceding embodiments, wherein the one or more at least bi-functional carboxylic acids, or cosmetically acceptable salts thereof, of the first formulation and of the second formulation are different.

Embodiment 10. The method according to any of the preceding embodiments, wherein step (b1) or (b2) occurs prior to step (c).

Embodiment 11. The method according to any of the preceding embodiments, wherein step (c) occurs prior to step (b1) or (b2).

Embodiment 12. The method according to any of the preceding embodiments, wherein at least one of said one or more at least bi-functional carboxylic acids has a molecular weight of less than 750 g/mol, particularly less than 600 g/mol, such as less than 500 g/mol.

Embodiment 13. The method according to any of the preceding embodiments, wherein said one or more at least bi-functional carboxylic acids have a molecular weight of less than 750 g/mol, particularly less than 600 g/mol, such as less than 500 g/mol.

Embodiment 14. The method according to any of the preceding embodiments, wherein the one or more at least bi-functional carboxylic acids are selected from the group consisting of Oxalic Acid, Malonic Acid, Succinic Acid, Glutaric Acid, Adipic Acid, Pimelic Acid, Suberic Acid, Azelaic Acid, Sebacic Acid, Maleic Acid, Fumaric Acid, Glutaconic Acid, Traumatic Acid, Muconic Acid, Glutinic Acid, Citraconic Acid, Mesaconic Acid, Malic Acid, Aspartic Acid, Glutamic Acid, Tartronic Acid, Tartaric Acid, Diaminopimelic Acid, Saccharic Acid, Mesoxalic Acid, Oxaloacetic Acid, Acetonedicarboxylic Acid, Arabinaric Acid, Phthalic Acid, Isophthalic Acid, Terephthalic Acid, Diphenic Acid, 2,6-Naphthalenedicarboxylic Acid, Citric Acid, Isocitric Acid, Aconitic Acid, Propane-1,2,3-tricarboxylic Acid, Trimesic Acid, Methanetetracarboxylic Acid, 1,2,3,4-Benzenetetracarboxylic Acid, 2,2'-(ethane-1,2-diylbis(azanediyl))disuccinic Acid, Aspergillomarasine Acid, Ethylenetetracarboxylic Acid, or derivatives thereof, or cosmetically acceptable salts thereof.

Embodiment 15. The method according to any of the preceding embodiments, wherein the one or more at least bi-functional carboxylic acid is selected from the group consisting of saturated aliphatic carboxylic acids having two, three of four carboxylic acids groups, a total number of carbon atoms of ten or less, optionally substituted with one or more methyl and/or hydroxyl groups, or cosmetically acceptable salts thereof.

Embodiment 16. The method according to any of the preceding embodiments, wherein the one or more at least bi-functional carboxylic acid is selected from the group consisting of Oxalic Acid, Malonic Acid, Succinic Acid, Glutaric Acid, Adipic Acid, Pimelic Acid, Suberic Acid, Azelaic Acid, Sebacic Acid, Malic Acid, Tartronic Acid, Tartaric Acid, Saccharic Acid, Arabinaric Acid, Citric Acid, Isocitric Acid, Propane-1,2,3-tricarboxylic Acid, or cosmetically acceptable salts thereof.

Embodiment 17. The method according to any of the preceding embodiments, wherein the one or more at least bi-functional carboxylic acid is selected from the group consisting of Malonic Acid, Succinic Acid, Glutaric Acid, Adipic Acid, Malic Acid, Tartaric Acid, Citric Acid, Isocitric Acid, Propane-1,2,3-tricarboxylic Acid, or cosmetically acceptable salts thereof, in particular malic acid or cosmetically acceptable salts thereof.

Embodiment 18. The method according to any of the preceding embodiments, wherein the first composition has a pH from 7.5 to 12, in particular a pH from 8.0 to 11, such as a pH from 8.5 to 10, or a pH from 9.0 to 10, or a pH from 9.1 to 10, or a pH from 9.2 to 10.

Embodiment 19. The method according to any of the preceding embodiments, wherein the second composition has a pH from 3.5 to 6.5, in particular a pH from 3.5 to 5.5, such as a pH from 4.0 to 5.0.

Embodiment 20. The method according to any of the preceding embodiments, wherein the first composition comprises from 0.1% to 25%, particularly from 1.0% to 18%, more particularly from 3.0% to 15%, such as 7.5% to 12%, of the one or more at least bi-functional carboxylic acids, or cosmetically acceptable salts thereof, by total weight of the first composition.

Embodiment 21. The method according to any of the preceding embodiments, wherein the mixed composition comprises from 0.01% to 5%, particularly from 0.1% to 2%, more particularly from 0.1% to 1.0%, such as 0.25% to 1.0%, of the one or more at least bi-functional carboxylic acids, or cosmetically acceptable salts thereof, by total weight of the mixed composition.

Embodiment 22. The method according to any of the preceding embodiments, wherein the second composition comprises from 0.1% to 25%, particularly from 0.5% to 15%, more particularly from 1.0% to 10%, such as 1.5% to 5.0%, of the one or more at least bi-functional carboxylic acids, or cosmetically acceptable salts thereof, by total weight of the second composition.

Embodiment 23. The method according to any of the preceding embodiments, wherein the first composition is left on the hair for 10-60 minutes, in particular 20-60 minutes, such as 30-45 minutes.

Embodiment 24. The method according to any of the preceding embodiments, wherein the second composition is left on the hair for 5-10 minutes.

Embodiment 25. The method according to any of the preceding embodiments, wherein the first composition is substantially free of, or free of, a further component selected from the group of diamines, polyamines, primary amines, fatty acids, silicones, oxidative dye precursors, direct dyes, reducing agents, unsaturated compounds having one or more carboxylic acid groups, and mixtures thereof.

Embodiment 26. The method according to any of the preceding embodiments, wherein the first composition is free of diamines, polyamines, primary amines, oxidative dye precursors, direct dyes, reducing agents, and unsaturated compounds having one or more carboxylic acid groups.

Embodiment 27. The method according to any of the preceding embodiments, wherein the second composition is substantially free of, or free of, a further component selected from the group of diamines, polyamines, primary amines, fatty acids, silicones, oxidative dye precursors, direct dyes, reducing agents, unsaturated compounds having one or more carboxylic acid groups, and mixtures thereof.

Embodiment 28. The method according to any of the preceding embodiments, wherein the second composition is free of diamines, polyamines, primary amines, oxidative dye precursors, direct dyes, reducing agents, and unsaturated compounds having one or more carboxylic acid groups.

Embodiment 29. The method according to any preceding embodiments, further comprising:
(d) rinsing, shampooing, conditioning the hair, or a combination thereof,
wherein step (d) occurs subsequent to step (b1) or (b2) and/or step (c).

Embodiment 30. The method according to embodiment 29, wherein the hair is dried after steps (c) or (d).

Embodiment 31. The method according to embodiment 30, wherein drying of the hair is carried out using a device selected from the group consisting of a hair dryer, a hair straightener, a curling iron, a hood, and combinations thereof.

Embodiment 32. The method according to any of the preceding embodiments, wherein the first composition is not for straightening hair.

Embodiment 33. The method according to any of the preceding embodiments, wherein the first composition is not used for straightening hair.

Embodiment 34. A method for treating hair comprising applying to the hair a first composition having a pH from 7 to 13, wherein said first composition comprises in a cosmetically acceptable carrier, one or more at least bi-functional carboxylic acids of Formula 1, or cosmetically acceptable salts thereof, or mixtures thereof, wherein Formula 1 is HOOC—Ra—(O—Rb)n-COOH, wherein Ra is selected from the group consisting of C1-C10 alkylene, C1-C10 cycloalkylene, C1-C10 alkenylene, C6 and C6-C12 (alkyl)arylene, Rb is C2-C4 alkylene, n is an integer from 0 to 4, wherein Ra and/or each Rb optionally are substituted with one or more substituents selected from —COOH, —OH, —NH2, —SH, and =O, and wherein the total number of carbon atoms in Ra plus Rb is 12 or less.

Embodiment 35. The method according to embodiment 34, wherein at least one of said one or more at least bi-functional carboxylic acids has a molecular weight of less than 750 g/mol, particularly less than 600 g/mol, such as less than 500 g/mol.

Embodiment 36. The method according to embodiment 34 or 35, wherein said one or more at least bi-functional carboxylic acids have a molecular weight of less than 750 g/mol, particularly less than 600 g/mol, such as less than 500 g/mol.

Embodiment 37. The method according to any of embodiments 34 to 36, wherein the one or more at least bi-functional carboxylic acids are selected from the group consisting of Oxalic Acid, Malonic Acid, Succinic Acid, Glutaric Acid, Adipic Acid, Pimelic Acid, Suberic Acid, Azelaic Acid, Sebacic Acid, Maleic Acid, Fumaric Acid, Glutaconic Acid, Traumatic Acid, Muconic Acid, Glutinic Acid, Citraconic Acid, Mesaconic Acid, Malic Acid, Aspartic Acid, Glutamic Acid, Tartronic Acid, Tartaric Acid, Diaminopimelic Acid, Saccharic Acid, Mesoxalic Acid, Oxaloacetic Acid, Acetonedicarboxylic Acid, Arabinaric Acid, Phthalic Acid, Isophthalic Acid, Terephthalic Acid, Diphenic Acid, 2,6-Naphthalenedicarboxylic Acid, Citric Acid, Isocitric Acid, Aconitic Acid, Propane-1,2,3-tricarboxylic Acid, Trimesic Acid, Methanetetracarboxylic Acid, 1,2,3,4-Benzenetetracarboxylic Acid, 2,2'-(ethane-1,2-diylbis(azanediyl))disuccinic Acid, Aspergillomarasine Acid, Ethylenetetracarboxylic Acid, or derivatives thereof, or cosmetically acceptable salts thereof.

Embodiment 38. The method according to any of embodiments 34 to 37, wherein the one or more at least bi-functional carboxylic acid is selected from the group consisting of saturated aliphatic carboxylic acids having two, three of four carboxylic acids groups, a total number of carbon atoms of ten or less, optionally substituted with one or more methyl and/or hydroxyl groups, or cosmetically acceptable salts thereof.

Embodiment 39. The method according to any of embodiments 34 to 38, wherein the one or more at least bi-functional carboxylic acid is selected from the group consisting of Oxalic Acid, Malonic Acid, Succinic Acid, Glutaric Acid, Adipic Acid, Pimelic Acid, Suberic Acid, Azelaic Acid, Sebacic Acid, Malic Acid, Tartronic Acid, Tartaric Acid, Saccharic Acid, Arabinaric Acid, Citric Acid, Isocitric Acid, Propane-1,2,3-tricarboxylic Acid, or cosmetically acceptable salts thereof.

Embodiment 40. The method according to any of embodiments 34 to 39, wherein the one or more at least bi-functional carboxylic acid is selected from the group consisting of Malonic Acid, Succinic Acid, Glutaric Acid, Adipic Acid, Malic Acid, Tartaric Acid, Citric Acid, Isocitric Acid, Propane-1,2,3-tricarboxylic Acid, or cosmetically acceptable salts thereof, in particular malic acid or cosmetically acceptable salts thereof.

Embodiment 41. The method according to any of embodiments 34 to 40, wherein the first composition has a pH from 7.5 to 12, in particular a pH from 8.0 to 11, such as a pH from 8.5 to 10, or a pH from 9.0 to 10, or a pH from 9.1 to 10, or a pH from 9.2 to 10.

Embodiment 42. The method according to any of embodiments 34 to 41, wherein the first composition comprises from 0.1% to 25%, particularly from 1.0% to 18%, more particularly from 3.0% to 15%, such as 7.5% to 12%, of the one or more at least bi-functional carboxylic acids, or cosmetically acceptable salts thereof, by total weight of the first composition.

Embodiment 43. The method according to any of embodiments 34 to 42, wherein the first composition is left on the hair for 10-60 minutes, in particular 20-60 minutes, such as 30-45 minutes.

Embodiment 44. The method according to any of embodiments 34 to 43, wherein the first composition is substantially free of, or free of, a further component selected from the group of diamines, polyamines, primary amines, fatty acids, silicones, oxidative dye precursors, direct dyes, reducing agents, unsaturated compounds having one or more carboxylic acid groups, and mixtures thereof.

Embodiment 45. The method according to any of embodiments 34 to 44, wherein the first composition is free of diamines, polyamines, primary amines, oxidative dye precursors, direct dyes, reducing agents, and unsaturated compounds having one or more carboxylic acid groups.

Embodiment 46. The method according to any of embodiments 34 to 45, wherein the first composition further is free of fatty acids and silicones.

Embodiment 47. The method according to any of embodiments 34 to 46, wherein a commercially available hair treatment composition comprising one of a bleaching agent, a coloring agent, and a permanent hair waving agent is applied to the hair simultaneously with the first composition or mixed with the first composition prior to applying to the hair.

Embodiment 48. The method according to embodiment 47, wherein the difference between the pH of the first composition and the pH of the hair treatment composition is 1.5 or less, particularly 1.2 or less, such as 1.0 or less.

Embodiment 49. The method according to embodiment 47 or 48, wherein the difference between the pH of the hair treatment composition and the pH of the mixed composition is 0.3 or less, particularly 0.2 or less, such as 0.15 or less.

Embodiment 50. The method according to any of embodiments 34 to 49, further comprising the step of rinsing, shampooing, conditioning the hair, or a combination thereof.

Embodiment 51. The method according to embodiment 50, wherein the hair is dried prior to or after the step of rinsing, shampooing, conditioning the hair, or a combination thereof.

Embodiment 52. The method according to embodiment 51, wherein drying of the hair is carried out using a device selected from the group consisting of a hair dryer, a hair straightener, a curling iron, a hood, and combinations thereof.

Embodiment 53. The method according to any of embodiments 34 to 52, wherein the first composition is not used for straightening hair.

Embodiment 54. The method according to any of embodiments 34 to 53, wherein the first composition is not for straightening hair.

Embodiment 55. A kit comprising:
(a) a first composition having a pH from 7 to 13;
(b) a second composition having a pH from 3 to 7;
wherein each of the first and the second composition comprises in a cosmetically acceptable carrier, one or more at least bi-functional carboxylic acids of Formula 1, or cosmetically acceptable salts thereof, or mixtures thereof,
wherein Formula 1 is HOOC—Ra—(O—Rb)n-COOH, wherein Ra is selected from the group consisting of C1-C10 alkylene, C1-C10 cycloalkylene, C1-C10 alkenylene, and C6-C12 (alkyl)arylene, Rb is C2-C4 alkylene, n is an integer from 0 to 4, wherein Ra and/or each Rb optionally are substituted with one or more substituents selected from —COOH, —OH, —NH2, —SH, and =O, and wherein the total number of carbon atoms in Ra plus Rb is 12 or less, wherein the first composition and the second composition are separately packaged.

Embodiment 56. The kit according to embodiment 55, wherein the one or more at least bi-functional carboxylic acids, or cosmetically acceptable salts thereof, of the first formulation and of the second formulation are identical.

Embodiment 57. The kit according to embodiment 55 or 56, wherein the one or more at least bi-functional carboxylic acids, or cosmetically acceptable salts thereof, of the first formulation and of the second formulation are different.

Embodiment 58. The kit according to any of embodiments 55 to 57, wherein at least one of said one or more at least bi-functional carboxylic acids has a molecular weight of less than 750 g/mol, particularly less than 600 g/mol, such as less than 500 g/mol.

Embodiment 59. The kit according to any of embodiments 55 to 58, wherein said one or more at least bi-functional carboxylic acids have a molecular weight of less than 750 g/mol, particularly less than 600 g/mol, such as less than 500 g/mol.

Embodiment 60. The kit according to any of embodiments 55 to 59, wherein the one or more at least bi-functional carboxylic acids are selected from the group consisting of Oxalic Acid, Malonic Acid, Succinic Acid, Glutaric Acid, Adipic Acid, Pimelic Acid, Suberic Acid, Azelaic Acid, Sebacic Acid, Maleic Acid, Fumaric Acid, Glutaconic Acid, Traumatic Acid, Muconic Acid, Glutinic Acid, Citraconic Acid, Mesaconic Acid, Malic Acid, Aspartic Acid, Glutamic Acid, Tartronic Acid, Tartaric Acid, Diaminopimelic Acid, Saccharic Acid, Mesoxalic Acid, Oxaloacetic Acid, Acetonedicarboxylic Acid, Arabinaric Acid, Phthalic Acid, Isophthalic Acid, Terephthalic Acid, Diphenic Acid, 2,6-Naphthalenedicarboxylic Acid, Citric Acid, Isocitric Acid, Aconitic Acid, Propane-1,2,3-tricarboxylic Acid, Trimesic Acid, Methanetetracarboxylic Acid, 1,2,3,4-Benzenetetracarboxylic Acid, 2,2'-(ethane-1,2-diylbis(azanediyl))disuccinic Acid, Aspergillomarasine Acid, Ethylenetetracarboxylic Acid, or derivatives thereof, or cosmetically acceptable salts thereof.

Embodiment 61. The kit according to any of embodiments 55 to 60, wherein the one or more at least bi-functional carboxylic acid is selected from the group consisting of saturated aliphatic carboxylic acids having two, three of four carboxylic acids groups, a total number of carbon atoms of ten or less, optionally substituted with one or more methyl and/or hydroxyl groups, or cosmetically acceptable salts thereof.

Embodiment 62. The kit according to any of embodiments 55 to 61, wherein the one or more at least bi-functional carboxylic acid is selected from the group consisting of Oxalic Acid, Malonic Acid, Succinic Acid, Glutaric Acid, Adipic Acid, Pimelic Acid, Suberic Acid, Azelaic Acid, Sebacic Acid, Malic Acid, Tartronic Acid, Tartaric Acid, Saccharic Acid, Arabinaric Acid, Citric Acid, Isocitric Acid, Propane-1,2,3-tricarboxylic Acid, or cosmetically acceptable salts thereof.

Embodiment 63. The kit according to any of embodiments 55 to 62, wherein the one or more at least bi-functional carboxylic acid is selected from the group consisting of Malonic Acid, Succinic Acid, Glutaric Acid, Adipic Acid, Malic Acid, Tartaric Acid, Citric Acid, Isocitric Acid, Propane-1,2,3-tricarboxylic Acid, or cosmetically acceptable salts thereof, in particular malic acid or cosmetically acceptable salts thereof.

Embodiment 64. The kit according to any of embodiments 55 to 63, wherein the first composition has a pH from 7.5 to 12, in particular a pH from 8.0 to 11, such as a pH from 8.5 to 10, or a pH from 9.0 to 10, or a pH from 9.1 to 10, or a pH from 9.2 to 10.

Embodiment 65. The kit according to any of embodiments 55 to 64, wherein the second composition has a pH from 3.5 to 6.5, in particular a pH from 3.5 to 5.5, such as a pH from 4.0 to 5.0.

Embodiment 66. The kit according to any of embodiments 55 to 65, wherein the first composition comprises from 0.1% to 25%, particularly from 1.0% to 18%, more particularly from 3.0% to 15%, such as 7.5% to 12%, of the one or more at least bi-functional carboxylic acids, or cosmetically acceptable salts thereof, by total weight of the first composition.

Embodiment 67. The kit according to any of embodiments 55 to 66, wherein the second composition comprises from 0.1% to 25%, particularly from 0.5% to 15%, more particularly from 1.0% to 10%, such as 1.5% to 5.0%, of the one or more at least bi-functional carboxylic acids, or cosmetically acceptable salts thereof, by total weight of the second composition.

Embodiment 68. The kit according to any of embodiments 55 to 67, wherein the first composition is substantially free of, or free of, a further component selected from the group of diamines, polyamines, primary amines, fatty acids, silicones, oxidative dye precursors, direct dyes, reducing agents, unsaturated compounds having one or more carboxylic acid groups, and mixtures thereof.

Embodiment 69. The kit according to any of embodiments 55 to 68, wherein the first composition is free of diamines, polyamines, primary amines, oxidative dye precursors, direct dyes, reducing agents, and unsaturated compounds having one or more carboxylic acid groups.

Embodiment 70. The kit according to any of embodiments 55 to 69, wherein the second composition is substantially free of, or free of, a further component selected from the group of diamines, polyamines, primary amines, fatty acids, silicones, oxidative dye precursors, direct dyes, reducing agents, unsaturated compounds having one or more carboxylic acid groups, and mixtures thereof.

Embodiment 71. The kit according to any of embodiments 55 to 70, wherein the second composition is free of diamines, polyamines, primary amines, oxidative dye precursors, direct dyes, reducing agents, and unsaturated compounds having one or more carboxylic acid groups.

Embodiment 72. The kit according to any of embodiments 55 to 71, further comprising at least one of a rinse, a shampoo, and a hair conditioner.

Embodiment 73. The kit according to any of embodiments 55 to 72, wherein the first composition is not for straightening hair.

Embodiment 74. The kit according to any of embodiments 55 to 73, wherein the first composition is not used for straightening hair.

Embodiment 75. The kit according to any of embodiments 55 to 74, further comprising a separately packaged hair treatment composition.

Embodiment 76. The kit according to embodiment 75, wherein the difference between the pH of the first composition and the pH of the hair treatment composition is 1.5 or less, particularly 1.2 or less, such as 1.0 or less.

Embodiment 77. The method according to embodiment 75 or 76, wherein the difference between the pH of the hair treatment composition and the pH of a composition mixed from the first composition and the hair treatment composition is 0.3 or less, particularly 0.2 or less, such as 0.15 or less.

Embodiment 78. The kit according to any of embodiments 75 to 77, wherein the hair treatment composition comprises one or more oxidizing agents.

Embodiment 79. The kit according to any of embodiments 75 to 78, wherein the hair treatment composition comprises oxidative dye precursors including one or more couplers and one or more primary intermediates.

Embodiment 80. The kit according to any of embodiments 75 to 79, wherein the hair treatment composition comprises one or more reducing agents.

Embodiment 81. Use of the kit according to any of embodiments 55 to 74 for restructuring hair or improving stressed hair or structurally damaged hair, and/or in a method for bleaching hair, highlighting hair, coloring hair, permanently waving hair, or a combination thereof.

Embodiment 82. Use of the kit according to any of embodiments 75 to 80 for restructuring hair, improving stressed hair or structurally damaged hair bleaching hair, highlighting hair, coloring hair, permanently waving hair, or a combination thereof.

Embodiment 83. The use according to embodiment 81 or 82, provided that the hair is not straightened hair.

Embodiment 84. A first composition for treating hair having a pH from 7 to 13, comprising in a cosmetically acceptable carrier, one or more at least bi-functional carboxylic acids of Formula 1, or cosmetically acceptable salts thereof, or mixtures thereof,
wherein Formula 1 is HOOC—Ra—(O—Rb)n-COOH, wherein Ra is selected from the group consisting of C1-C10 alkylene, C1-C10 cycloalkylene, C1-C10 alkenylene, and C6-C12 (alkyl)arylene, Rb is C2-C4 alkylene, n is an integer from 0 to 4, wherein Ra and/or each Rb optionally are substituted with one or more substituents selected from —COOH, —OH, —NH2, —SH, and =O, and wherein the total number of carbon atoms in Ra plus Rb is 12 or less.

Embodiment 85. The first composition according to embodiment 84, wherein at least one of said one or more at least bi-functional carboxylic acids has a molecular weight of less than 750 g/mol, particularly less than 600 g/mol, such as less than 500 g/mol.

Embodiment 86. The first composition according to embodiment 84 or 85, wherein said one or more at least bi-functional carboxylic acids have a molecular weight of less than 750 g/mol, particularly less than 600 g/mol, such as less than 500 g/mol.

Embodiment 87. The first composition according to any of embodiments 84 to 86, wherein the one or more at least bi-functional carboxylic acids are selected from the group consisting of Oxalic Acid, Malonic Acid, Succinic Acid, Glutaric Acid, Adipic Acid, Pimelic Acid, Suberic Acid, Azelaic Acid, Sebacic Acid, Maleic Acid, Fumaric Acid, Glutaconic Acid, Traumatic Acid, Muconic Acid, Glutinic Acid, Citraconic Acid, Mesaconic Acid, Malic Acid, Aspartic Acid, Glutamic Acid, Tartronic Acid, Tartaric Acid, Diaminopimelic Acid, Saccharic Acid, Mesoxalic Acid, Oxaloacetic Acid, Acetonedicarboxylic Acid, Arabinaric Acid, Phthalic Acid, Isophthalic Acid, Terephthalic Acid, Diphenic Acid, 2,6-Naphthalenedicarboxylic Acid, Citric Acid, Isocitric Acid, Aconitic Acid, Propane-1,2,3-tricarboxylic Acid, Trimesic Acid, Methanetetracarboxylic Acid, 1,2,3,4-Benzenetetracarboxylic Acid, 2,2'-(ethane-1,2-diylbis(azanediyl))disuccinic Acid, Aspergillomarasine Acid, Ethylenetetracarboxylic Acid, or derivatives thereof, or cosmetically acceptable salts thereof.

Embodiment 88. The first composition according to any of embodiments 84 to 87, wherein the one or more at least bi-functional carboxylic acid is selected from the group consisting of saturated aliphatic carboxylic acids having two, three of four carboxylic acids groups, a total number of carbon atoms of ten or less, optionally substituted with one or more methyl and/or hydroxyl groups, or cosmetically acceptable salts thereof.

Embodiment 89. The first composition according to any of embodiments 84 to 88, wherein the one or more at least bi-functional carboxylic acid is selected from the group consisting of Oxalic Acid, Malonic Acid, Succinic Acid, Glutaric Acid, Adipic Acid, Pimelic Acid, Suberic Acid, Azelaic Acid, Sebacic Acid, Malic Acid, Tartronic Acid, Tartaric Acid, Saccharic Acid, Arabinaric Acid, Citric Acid, Isocitric Acid, Propane-1,2,3-tricarboxylic Acid, or cosmetically acceptable salts thereof.

Embodiment 90. The first composition according to any of embodiments 84 to 89, wherein the one or more at least bi-functional carboxylic acid is selected from the group consisting of Malonic Acid, Succinic Acid, Glutaric Acid, Adipic Acid, Malic Acid, Tartaric Acid, Citric Acid, Isocitric Acid, Propane-1,2,3-tricarboxylic Acid, or cosmetically acceptable salts thereof, in particular malic acid or cosmetically acceptable salts thereof.

Embodiment 91. The first composition according to any of embodiments 84 to 90, wherein the first composition has a pH from 7.5 to 12, in particular a pH from 8.0 to 11, such as a pH from 8.5 to 10, or a pH from 9.0 to 10, or a pH from 9.1 to 10, or a pH from 9.2 to 10.

Embodiment 92. The first composition according to any of embodiments 84 to 91, wherein the first composition comprises from 0.1% to 25%, particularly from 1.0% to 18%, more particularly from 3.0% to 15%, such as 7.5% to 12%, of the one or more at least bi-functional carboxylic acids, or cosmetically acceptable salts thereof, by total weight of the first composition.

Embodiment 93. The first composition according to any of embodiments 84 to 92, wherein the first composition is substantially free of, or free of, a further component selected from the group of diamines, polyamines, primary amines, fatty acids, silicones, oxidative dye precursors, direct dyes, reducing agents, unsaturated compounds having one or more carboxylic acid groups, and mixtures thereof.

Embodiment 94. The first composition according to any of embodiments 84 to 93, wherein the first composition is free of diamines, polyamines, primary amines, oxidative dye precursors, direct dyes, reducing agents, and unsaturated compounds having one or more carboxylic acid groups.

Embodiment 95. The first composition according to any of embodiments 84 to 94, wherein the first composition is not for straightening hair.

Embodiment 96. The first composition according to any of embodiments 84 to 95, wherein the first composition is not used for straightening hair.

Embodiment 97. A kit comprising the first composition according to any of embodiments 84 to 96 and a hair treatment composition, wherein the first composition and the hair treatment are separately packaged.

Embodiment 98. The kit according to embodiment 97, wherein the difference between the pH of the first composition and the pH of the hair treatment composition is 1.5 or less, particularly 1.2 or less, such as 1.0 or less.

Embodiment 99. The method according to embodiment 97 or 98, wherein the difference between the pH of the hair treatment composition and the pH of a composition mixed from the first composition and the hair treatment composition is 0.3 or less, particularly 0.2 or less, such as 0.15 or less.

Embodiment 100. The kit according to any of embodiments 97 to 99, wherein the hair treatment composition comprises one or more oxidizing agents.

Embodiment 101. The kit according to any of embodiments 97 to 100, wherein the hair treatment composition comprises oxidative dye precursors including one or more couplers and one or more primary intermediates.

Embodiment 102. The kit according to any of embodiments 97 to 101, wherein the hair treatment composition comprises one or more reducing agents.

Embodiment 103. The kit according to any of embodiments 97 to 102, further comprising at least one of a rinse, a shampoo, and a hair conditioner.

Embodiment 104. Use of first composition according to any of embodiments 84 to 96 for restructuring hair or improving stressed hair or structurally damaged hair, and/or in a method for bleaching hair, highlighting hair, coloring hair, permanently waving hair, or a combination thereof.

Embodiment 105. Use of the kit according to any of embodiments 97 to 103 for restructuring hair, improving stressed hair or structurally damaged hair, bleaching hair, highlighting hair, coloring hair, permanently waving hair, or a combination thereof.

Embodiment 106. The use according to embodiment 104 or 105, provided that the hair is not straightened hair.

What is claimed is:

1. A method for treating hair comprising the steps of:
   (a) mixing a first composition having a pH from 7 to 13 with a hair treatment composition to form a mixed composition, the hair treatment composition comprising one of a bleaching agent, a coloring agent, and a permanent hair waving agent;
   (b1) applying to the hair the mixed composition having a pH from 7 to 13; and
   (c) applying to the hair a second composition having a pH from 3 to 7, wherein
   each of the first composition and the second composition comprises in a cosmetically acceptable carrier, one or more at least bi-functional carboxylic acids of Formula 1, or cosmetically acceptable salts thereof, or mixtures thereof;
   wherein Formula 1 is HOOC—Ra-(O—Rb)n-COOH, wherein Ra is selected from the group consisting of C1-C10 alkylene, C1-C10 cycloalkylene, C1-C10 alkenylene, C6-C12 (alkyl)arylene, Rb is C2-C4 alkylene, n is an integer from 0 to 4 and wherein the total number of carbon atoms in Ra plus Rb is 12 or less.

2. The method of claim 1, wherein a difference between the pH of the first composition and the pH of the hair treatment composition is 1.5 or less.

3. The method of claim 1, wherein a difference between the pH of the hair treatment composition and the pH of the mixed composition is 0.3 or less.

4. The method of claim 1, wherein the hair treatment composition comprises one or more oxidizing agents, oxidative dye precursors including one or more couplers and one or more primary intermediates, or both oxidizing agent(s) and oxidative dye precursors.

5. The method of claim 1, wherein the hair treatment composition comprises one or more reducing agents.

6. The method of claim 1, wherein the one or more at least bi-functional carboxylic acid of the first composition and of the second composition are identical.

7. The method of claim 1, wherein the one or more at least bi-functional carboxylic acid is selected from the group consisting of Oxalic Acid, Malonic Acid, Succinic Acid, Glutaric Acid, Adipic Acid, Pimelic Acid, Suberic Acid, Azelaic Acid, Sebacic Acid, Maleic Acid, Fumaric Acid, Glutaconic Acid, Traumatic Acid, Muconic Acid, Glutinic Acid, Citraconic Acid, Mesaconic Acid, Malic Acid, Aspartic Acid, Glutamic Acid, Tartronic Acid, Tartaric Acid, Diaminopimelic Acid, Saccharic Acid, Mesoxalic Acid, Oxaloacetic Acid, Acetonedicarboxylic Acid, Arabinaric Acid, Phthalic Acid, Isophthalic Acid, Terephthalic Acid, Diphenic Acid, 2,6-Naphthalenedicarboxylic Acid, Citric Acid, Isocitric Acid, Aconitic Acid, Propane-1,2,3-tricarboxylic Acid, Trimesic Acid, Methanetetracarboxylic Acid, 1,2,3,4-Benzenetetracarboxylic Acid, 2,2'-(ethane-1,2-diyl-bis(azanediyl))disuccinic Acid, Aspergillomarasine Acid, Ethylenetetracarboxylic Acid, or derivatives thereof, or cosmetically acceptable salts thereof.

8. The method of claim 1, wherein the first composition comprises from 0.1% to 25% of the one or more at least bi-functional carboxylic acid, or cosmetically acceptable salt thereof, by total weight of the first composition, and/or wherein the second composition comprises from 0.1% to 25% of the one or more at least bi-functional carboxylic acid, or cosmetically acceptable salt thereof, by total weight of the second composition.

9. The method of claim 1, wherein the first composition has a pH from 7.5 to 12 and/or wherein the second composition has a pH from 3.5 to 6.5.

10. The method of claim 1, wherein the first composition is substantially free of, or free of, a further component selected from the group of diamines, polyamines, primary amines, fatty acids, silicones, oxidative dye precursors, direct dyes, reducing agents, unsaturated compounds having one or more carboxylic acid groups, and mixtures thereof.

11. The method of claim 1, further comprising:
   (d) rinsing, shampooing, conditioning the hair, or a combination thereof, wherein step (d) occurs subsequent to step (bl) and/or step (c), and optionally
   (e) drying the hair after step (c) and (d).

12. A kit comprising:
   (1) a first composition having a pH from 7 to 13;
   (2) a second composition having a pH from 3 to 7;
   wherein each of the first and the second composition comprises in a cosmetically acceptable carrier, one or more at least bi-functional carboxylic acids of Formula 1, or cosmetically acceptable salts thereof, or mixtures thereof;
   wherein Formula 1 is HOOC—Ra-(O—Rb)n-COOH, wherein Ra is selected from the group consisting of C1-C10 alkylene, C1-C10 cycloalkylene, C1-C10 alkenylene, C6-C12 (alkyl)arylene, Rb is C2-C4 alkylene, n is an integer from 0 to 4, and wherein the total number of carbon atoms in Ra plus Rb is 12 or less;
   wherein the first composition, and the second composition are, separately packaged.

13. The method of claim 1, wherein the difference between the pH of the first composition and the pH of the hair treatment composition is 1.2 or less.

14. The method of claim 1, wherein the difference between the pH of the hair treatment composition and the pH of the mixed composition is 0.2 or less.

15. The method of claim 1, wherein the first composition comprises from 1.0% to 18% of the one or more at least bi-functional carboxylic acid, or cosmetically acceptable salt thereof, by total weight of the first composition, and/or wherein the second composition comprises 0.5% to 15% of the one or more at least bi-functional carboxylic acid, or cosmetically acceptable salt thereof, by total weight of the second composition.

16. The method according to claim 1, wherein the first composition has a pH from 8.0 to 11 and/or wherein the second composition has a pH from 3.5 to 5.5.

17. The method of claim 1, wherein at least one of Ra and Rb is optionally substituted with one or more substituents selected from —COOH, —OH, —NH2, —SH, and =O.

18. The method of claim 12, wherein at least one of Ra and Rb is optionally substituted with one or more substituents selected from —COOH, —OH, —NH2, —SH, and =O.

* * * * *